(12) United States Patent
Welcher et al.

(10) Patent No.: US 7,811,791 B2
(45) Date of Patent: Oct. 12, 2010

(54) INTERFERON-LIKE MOLECULES AND USES THEREOF

(75) Inventors: Andrew Welcher, Ventura, CA (US); Duanzhi Wen, Thousand Oaks, CA (US); Michael Kelly, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 821 days.

(21) Appl. No.: 10/977,680

(22) Filed: Oct. 29, 2004

(65) Prior Publication Data

US 2005/0221344 A1 Oct. 6, 2005

Related U.S. Application Data

(63) Continuation of application No. 09/724,860, filed on Nov. 28, 2000, now abandoned.

(60) Provisional application No. 60/169,720, filed on Dec. 8, 1999.

(51) Int. Cl.
C12N 15/00 (2006.01)
C12N 5/00 (2006.01)
C12P 21/00 (2006.01)
C07H 21/04 (2006.01)

(52) U.S. Cl. ............... 435/69.51; 536/23.52; 435/69.1; 435/70.1; 435/71.1; 435/320.1; 435/325

(58) Field of Classification Search ................ None
See application file for complete search history.

(56) References Cited

U.S. PATENT DOCUMENTS

| 4,902,618 | A | 2/1990 | Berg |
| 5,480,981 | A | 1/1996 | Goodwin et al. |
| 6,433,145 | B1 * | 8/2002 | LaFleur et al. ............... 530/351 |
| 6,472,512 | B1 | 10/2002 | LaFleur et al. |
| 7,390,637 | B2 | 6/2008 | LaFleur et al. |

FOREIGN PATENT DOCUMENTS

| WO | 00/05371 | 2/2000 |
| WO | 00/55324 | 9/2000 |
| WO | 01/07608 | 2/2001 |

OTHER PUBLICATIONS

Wells, Aditivity of Mutational Effects in Proteins, 1990, Biochemistry, vol. 26, No. 37, pp. 8509-8517.*
Ngo et al., 1994, The Protein Folding Problem and Tertiary Structure Prediction, pp. 492-495.*
Bork, A. Powers and pitfalls in sequence aalysis: the 70% hurdle, (2000), Genome Res.10: pp. 398-400.*
Skolnick et al. From genes to protein structure and function:novel application of computational approches in the genomic era (2000), TIBTECH, vol. 18(1), pp. 34-39.*
Cao et al., Homo sapiens interferon-like protein precursor, mRNA, complete cds, Homo sapeins, GenBank Acc. No. AF146759, May 4, 2000.
Colamonici et al., "Direct Binding to and Tyrosine Phosphorylation of the alpha Subunit of the Type I Interferon Receptor by p135tyk2 Tyrosine Kinase," Mol. Cell. Biol. 14(12):8133-42 (1994).
E.caballus IFN-omega 2, Equus caballus (horse), GenBank Acc. No. A33695, Jun. 19, 1996.
Gilmour et al., "Signal Transduction and Activation of Gene Transcription by Interferons," Gene Expr. 5:1-18 (1995).
Hansen et al., Trophoblast interferon 4 precursor (clone bTP4)—bovine, Bos taurus (cow), GenBank Acc. No. A39505, Jul. 16,1999.
Heim, "The Jak-STAT Pathway: Cytokine Signalling from the Receptor to the Nucleus," J. Recept. Signal Transduct. Res. 19:75-120 (1999).
Himmler et al., Equus caballus IFN-alpha2, GenBank Acc. No. CAA01258, Oct. 3, 1994.
Ihle, " The Janus kinase family and signaling through members of the cytokine receptor superfamily," Proc. Soc. Exp. Biol. Med. 206(3):268-72 (1994).
Imakawa et al., Bos Taurus Trophoblast protein-1, GenBank Acc. No. AAA50459, Oct. 12, 1994.
LaFleur et al., "Interferon-kappa, a Novel Type I Interferon Expressed in Human Keratinocytes," J. Biol. Chem. 276 (43): 39765-71 (2001).
LaFleur et al., Synthetic construct human interferon kappa precursor, GenBank Acc. No. AF384047, Oct. 23, 2001.
LaFleur et al., Homo sapiens interferon kappa precursor, GenBank Acc. No. AF384048, Oct. 23, 2001.
Larner et al., "Interferon Signal Transduction," Biotherapy 8:175-81 (1996).
Lee et al., Rattus sp. EST222724, EMBL-EBI ID No. AI179042, Jan. 22, 1999.
Lefevre et al., "A Novel and Atypical Type One Interferon Gene Expressed by Trophoblast during Early Pregnancy," J. Biol. Chem. 268(26):19760-68 (1993).
Marra et al., Mus musculus cDNA clone, GenBank Acc. No. AI155872, Sep. 30, 1998.
Mege et al., "The Porcine Family of Interferon-omega: Cloning, Structural Analysis, and Functional Studies of Five Related Genes," J. Interferon Res. 11(6):341-50 (1991).
NCBI Annotation Project, Homo sapiens interferon kappa precursor, GenBank Acc. No. XM_035950, Feb. 7, 2002.
Pesta, "The Interferon Receptors," Semin. Oncol. 24(3 Suppl. 9):S9-18-S9-40 (1997).
Sambrook et al., Molecular Cloning: A Laboratory Manual 6.59-6.60 (3rd ed. 2001).
Shuai, "Interferon-activated signal transduction to the nucleus," Curr. Opin. Cell Biol. 6:253-59 (1994).

(Continued)

Primary Examiner—Christine J Saoud
Assistant Examiner—Jegatheesan Seharaseyon
(74) Attorney, Agent, or Firm—John Lamerdin

(57) ABSTRACT

The present invention provides Interferon-Like (IFN-L) polypeptides and nucleic acid molecules encoding the same. The invention also provides selective binding agents, vectors, host cells, and methods for producing IFN-L polypeptides. The invention further provides pharmaceutical compositions and methods for the diagnosis, treatment, amelioration, and/or prevention of diseases, disorders, and conditions associated with IFN-L polypeptides.

12 Claims, 10 Drawing Sheets

OTHER PUBLICATIONS

Silvennoinen et al., "Interferon-induced nuclear signalling by Jak protein tyrosine kinases," Nature 366 (6455):583-85 (1993).

Soares, Rattus norvegicus EST, GenBank Acc. No. AA998549, Jun. 5, 1998.

Stark et al., "How Cells Respond to Interferons," Annu. Rev. Biochem. 67:227-64 (1998).

Stewart et al., Bos taurus trophoblast interferon type I precursor, GenBank Acc. No. S23751, Jul. 16,1999.

Williams et al., "Interacting Pathways of Interferon Signling," Semin. Oncol. 24(3 Suppl. 9):S9-70-S9-77 (1997).

Zhang et al., Homo sapiens interferon kappa precursor, GenBank NP_064509.1, Oct. 17, 2005.

* cited by examiner

FIG. 1A

```
gggtgttgta gatattttc ctttggaaga aatactgagc accaaggctg ag atg aca    58
                                                        Met Thr
                                                         1 ctg aag tat tta tgg ctg gtg gcc ctc gtg gct cta tac att tca ccc   106
Leu Lys Tyr Leu Trp Leu Val Ala Leu Val Ala Leu Tyr Ile Ser Pro
         5                  10                  15 atc cag tct cag aac tgt gtg tat ctg gat cat acc atc ttg gaa aac   154
Ile Gln Ser Gln Asn Cys Val Tyr Leu Asp His Thr Ile Leu Glu Asn
        20                  25                  30 atg aaa ctt ctg agc agc atc agg acc acc ttt ccc tta aga tgt cta   202
Met Lys Leu Leu Ser Ser Ile Arg Thr Thr Phe Pro Leu Arg Cys Leu
 35                  40                  45                  50 aaa gat atc acg gat ttt gag ttt cct caa gag att ctg ctg tac gtc   250
Lys Asp Ile Thr Asp Phe Glu Phe Pro Gln Glu Ile Leu Leu Tyr Val
                     55                  60                  65 cag cat gtg aaa aag gac ata aag gca gtc acc tat cat ata tct tct   298
Gln His Val Lys Lys Asp Ile Lys Ala Val Thr Tyr His Ile Ser Ser
                 70                  75                  80 ctg gcg cta att att ttc agt ctt aaa gac tcc atc tcc ctg gcg aca   346
Leu Ala Leu Ile Ile Phe Ser Leu Lys Asp Ser Ile Ser Leu Ala Thr
             85                  90                  95 gag gaa cgc ttg gaa cgt atc aga tcg gga ctt ttc aaa caa gtg cag   394
Glu Glu Arg Leu Glu Arg Ile Arg Ser Gly Leu Phe Lys Gln Val Gln
100                 105                 110 caa gct cga gag tgc atg gta gac gag gag aac aag aac acg gag gag   442
Gln Ala Arg Glu Cys Met Val Asp Glu Glu Asn Lys Asn Thr Glu Glu
115                 120                 125                 130 gac agt aca tca caa cat cct cac tca gag ggc ttc aag gca gtc tac   490
Asp Ser Thr Ser Gln His Pro His Ser Glu Gly Phe Lys Ala Val Tyr
                135                 140                 145 ctg gaa ttg aac aag tat ttc ttc aga atc aga aag ttc ctg gta aat   538
Leu Glu Leu Asn Lys Tyr Phe Phe Arg Ile Arg Lys Phe Leu Val Asn
                150                 155                 160 aag aaa tac agt ttc tgt gcc tgg aag att gtc gtg gtg gaa ata aga   586
Lys Lys Tyr Ser Phe Cys Ala Trp Lys Ile Val Val Val Glu Ile Arg
            165                 170                 175 aga tgt ttc agt ata ttt tac aaa cta ctc aac atg aat tgagaatcat   635
Arg Cys Phe Ser Ile Phe Tyr Lys Leu Leu Asn Met Asn
180                 185                 190 ccagcttcaa gcaagaactt agatagaagt tgtgactgct caaatgtccc caagaacgct  695
```

FIG. 1B

```
tgattctaag gctattgcga gtctgctgct acacacttcg gacgcaagac ttttcaaggt    755
cagggttcaa ggtagtacag tcaaaggaag tcttatgtta agcaaaagaa aaatttcagt    815
ggaaaagcta gcagaaatgt caacttgtca aaaaaacaac ttatggatta tggcattgac    875
gttactagca aaaaaataa aacaaaaaaa aacaaaaa                              913
```

FIG. 2A

```
aagcttaatt taacaaaatt ggaaaaacct aaactatact gtgctctggt gacctagcaa  60
tcaaataatc acagtcattt ggtcaatgtc tatgattaac tcaatgagac aggatgtttg 120
gctatagcac caggtacaaa aaatatattt tcatgaagga tcactccctc ttatgtaata 180
gatttgggtg agtgagtgag tgagtgagtg catggactca cagcttttgg ctttctgaaa 240
taccctgcat cagtcttgtt atgatgattc cttagtgctg ggatggatca tccaggcatt 300
taaggtaaca cgatggtaat tctttgctca tttttcaggg aaaaaaaaaa gttatcactt 360
ccaaagtcgg catagtcacc cgaagtaaaa aaaaaaaaaa aaaaaaaaag cctcagaggc 420 aaggaaagg ggccgcaacc ttggttaact gtgaaatgac gaatgagaaa actcctcctg 480
ctgaagatat tcaggtatat aaaggcacat gaaggaaaac tcaaaacatc attgtcatat 540
acacatcttc tggattttt agcttgcaaa aaaa atg agc acc aaa cct gat atg 595
                                    Met Ser Thr Lys Pro Asp Met
                                      1                   5
```

| | | | | | | | | | | | | |
|---|---|---|---|---|---|---|---|---|---|---|---|---|
| att | caa | aag | tgt | ttg | tgg | ctt | gag | atc | ctt | atg | ggt | ata | ttc | att | gct | 643 |
| Ile | Gln | Lys | Cys | Leu | Trp | Leu | Glu | Ile | Leu | Met | Gly | Ile | Phe | Ile | Ala | |
| | | 10 | | | | | 15 | | | | 20 | | | | | |

```
att caa aag tgt ttg tgg ctt gag atc ctt atg ggt ata ttc att gct   643
Ile Gln Lys Cys Leu Trp Leu Glu Ile Leu Met Gly Ile Phe Ile Ala
         10                  15                  20 ggc acc cta tcc ctg gac tgt aac tta ctg aac gtt cac ctg aga aga   691
Gly Thr Leu Ser Leu Asp Cys Asn Leu Leu Asn Val His Leu Arg Arg
         25                  30                  35 gtc acc tgg caa aat ctg aga cat ctg agt agt atg agc aat tca ttt   739
Val Thr Trp Gln Asn Leu Arg His Leu Ser Ser Met Ser Asn Ser Phe
 40              45                  50                  55 cct gta gaa tgt cta cga gaa aac ata gct ttt gag ttg ccc caa gag   787
Pro Val Glu Cys Leu Arg Glu Asn Ile Ala Phe Glu Leu Pro Gln Glu
             60                  65                  70 ttt ctg caa tac acc caa cct atg aag agg gac atc aag aag gcc ttc   835
Phe Leu Gln Tyr Thr Gln Pro Met Lys Arg Asp Ile Lys Lys Ala Phe
                 75                  80                  85 tat gaa atg tcc cta cag gcc ttc aac atc ttc agc caa cac acc ttc   883
Tyr Glu Met Ser Leu Gln Ala Phe Asn Ile Phe Ser Gln His Thr Phe
                 90                  95                 100 aaa tat tgg aaa gag aga cac ctc aaa caa atc caa ata gga ctt gat   931
Lys Tyr Trp Lys Glu Arg His Leu Lys Gln Ile Gln Ile Gly Leu Asp
            105                 110                 115 cag caa gca gag tac ctg aac caa tgc ttg gag gaa gac gag aat gaa   979
Gln Gln Ala Glu Tyr Leu Asn Gln Cys Leu Glu Glu Asp Glu Asn Glu
120                 125                 130                 135
```

FIG. 2B

```
aat gaa gac atg aaa gaa atg aaa gag aat gag atg aaa ccc tca gaa    1027
Asn Glu Asp Met Lys Glu Met Lys Glu Asn Glu Met Lys Pro Ser Glu
            140             145             150 gcc agg gtc ccc cag ctg agc agc ctg gaa ctg agg aga tat ttc cac    1075
Ala Arg Val Pro Gln Leu Ser Ser Leu Glu Leu Arg Arg Tyr Phe His
            155             160             165 agg ata gac aat ttc ctg aaa gaa aag aaa tac agt gac tgt gcc tgg    1123
Arg Ile Asp Asn Phe Leu Lys Glu Lys Lys Tyr Ser Asp Cys Ala Trp
            170             175             180 gag att gtc cga gtg gaa atc aga aga tgt ttg tat tac ttt tac aaa    1171
Glu Ile Val Arg Val Glu Ile Arg Arg Cys Leu Tyr Tyr Phe Tyr Lys
    185             190             195 ttt aca gct cta ttc agg agg aaa taaggtatat ttttggaatt aaaattcctt   1225
Phe Thr Ala Leu Phe Arg Arg Lys
200             205 ttccctccga aatctctttc tccttctcct cctccatctt cttttaagg attgttgtgc   1285 tgtcctgtaa gcctgtcctc agttggactg gtagcctcgg aacatcaggg acactcacct  1345
ctctaaggag aggtaatgcc aaccatcctc agggtgacca agagtctcct tagaaagtct  1405
ttaagacatt tttaaggaa taagattccc tctccgtctt cttctattct ctcttgctct   1465
tttctgtggc cattttgaaa gagctttgct atatatacca cctgtggact tcaccaagac  1525
aatggctaga ggatagggag cagagaatgt tgcaaaatgg taacatttca atgacttaac  1585
tgttttgctg ccaaggttgc ttatcctatg aaaattcagc acattaaaag agcttataca  1645
tgctccctag agtcaatact cttgcatttt ccccctcctg ctcgggggga aaaggttga   1705 catttctggc ccatttcctt ctcagcttgg tttgtttgaa tgatgcttg tggaatggta   1765 tttcattact ttaagagtga agatccatag tgaaattgga tggatggttg aattagacga  1825
ccattaagct t                                                       1836
```

FIG. 3

```
            1                                                           50
huIFN-L     MSTKPDMIQK CLWLEILMGI FIAGTLSLDC NLLNVHLRRV TWQNLRHLSS
raIFN-L     ~~~~~~MTLK YLWLVALVAL YISPIQSQNC ....VYLDHT ILENMKLLSS
huIFN-β     ~~~~~~MTNK CLLQIALLLC FSTTALSMSY NLLGFLQRSS NFQCQKLLWQ
cons        ------MT-K CWWL-AL--- FI---LS--C NLL-V-LR-- --QN-KLLSS 51                                                          100
huIFN-L     MSNSFPVECL RENIAFELPQ EFLQYTQPMK RDIKKAFYEM SLQAFNIFS.
raIFN-L     IRTTFPLRCL KDITDFEFPQ EILLYVQHVK KDIKAVTYHI SSLALIIFSL
huIFN-β     LNGRLEY.CL KDRMNFDIPE EIKQLQQFQK EDAALTIYEM LQNIFAIFRQ
cons        ----FP--CL KD---FE-PQ EILQY-Q--K -DIK---YEM S--AF-IFS- 101                                                         150
huIFN-L     QHTFKYWKER HLKQIQIGLD QQAEYLNQCL EEDENENEDM KEMKENEMKP
raIFN-L     KDSISLATEE RLERIRSGLF KQVQQARECM VDEENKNTE. .EDSTSQHPH
huIFN-β     DSSSTGWNET IVENLLANVY HQINHLKTVL .EEKLEKEDF TRGK......
cons        --S---W-E- -LE-I--GL- -Q---L--CL -EEENENED- -E-K------

151                                                         200
huIFN-L     SEARVPQLSS LELRRYFHRI DNFLKEKKYS DCAWEIVRVE IRRCLYYFYK
raIFN-L     SEGF..KAVY LELNKYFFRI RKFLVNKKYS FCAWKIVVVE IRRCFSIFYK
huIFN-β     ......LMSS LHLKRYYGRI LHYLKAKEYS HCAWTIVRVE ILRNFYFINR
cons        SE------SS LEL-RYF-RI --FLK-KKYS -CAW-IVRVE IRRCFY-FYK 201
huIFN-L     FTALFRRK
raIFN-L     LLNMN~~~
huIFN-β     LTGYLRN~
cons        LT---R--
```

FIG. 4

| | | | | | | | | | | | | | | | | |
|---|---|---|---|---|---|---|---|---|---|---|---|---|---|---|---|---|
| cat | atg | tgt | gta | tat | ctc | gat | cat | act | atc | ttg | gag | aat | atg | aaa | ctt | 48 |
| | Met | Cys | Val | Tyr | Leu | Asp | His | Thr | Ile | Leu | Glu | Asn | Met | Lys | Leu | |
| | 1 | | | | 5 | | | | | 10 | | | | | 15 | |

```
ctg agc agc atc cgt acc acc ttt cct ctg cgt tgt ctg aaa gat atc     96
Leu Ser Ser Ile Arg Thr Thr Phe Pro Leu Arg Cys Leu Lys Asp Ile
                20                      25                  30 acg gat ttt gag ttt cct caa gag att ctg ctg tac gtc cag cat gtg    144
Thr Asp Phe Glu Phe Pro Gln Glu Ile Leu Leu Tyr Val Gln His Val
            35                      40                  45 aaa aag gac ata aag gca gtc acc tat cat ata tct tct ctg gcg cta    192
Lys Lys Asp Ile Lys Ala Val Thr Tyr His Ile Ser Ser Leu Ala Leu
        50                      55                  60 att att ttc agt ctt aaa gac tcc atc tcc ctg gcg aca gag gaa cgc    240
Ile Ile Phe Ser Leu Lys Asp Ser Ile Ser Leu Ala Thr Glu Glu Arg
    65                      70                  75 ttg gaa cgt atc aga tcg gga ctt ttc aaa caa gtg cag caa gct cga    288
Leu Glu Arg Ile Arg Ser Gly Leu Phe Lys Gln Val Gln Gln Ala Arg
 80                      85                  90                  95 gag tgc atg gta gac gag gag aac aag aac acg gag gag gac agt aca    336
Glu Cys Met Val Asp Glu Glu Asn Lys Asn Thr Glu Glu Asp Ser Thr
                100                     105                 110 tca caa cat cct cac tca gag ggc ttc aag gca gtc tac ctg gaa ttg    384
Ser Gln His Pro His Ser Glu Gly Phe Lys Ala Val Tyr Leu Glu Leu
            115                     120                 125 aac aag tat ttc ttc aga atc aga aag ttc ctg gta aat aag aaa tac    432
Asn Lys Tyr Phe Phe Arg Ile Arg Lys Phe Leu Val Asn Lys Lys Tyr
        130                     135                 140 agt ttc tgt gcc tgg aag att gtc gtg gtg gaa att cgt cgt tgt ttc    480
Ser Phe Cys Ala Trp Lys Ile Val Val Val Glu Ile Arg Arg Cys Phe
    145                     150                 155 agt att ttt tac aaa ctg ctg aac atg aat taatggatcc                 520
Ser Ile Phe Tyr Lys Leu Leu Asn Met Asn
160                     165
```

FIG. 5

```
cat atg tgt gta tat ctc gat cat act atc ttg gag aat atg aaa ctt    48
    Met Cys Val Tyr Leu Asp His Thr Ile Leu Glu Asn Met Lys Leu
    1               5                   10                  15 ctg agc agc atc cgt acc acc ttt cct ctg cgt tgt ctg aaa gat atc    96
Leu Ser Ser Ile Arg Thr Thr Phe Pro Leu Arg Cys Leu Lys Asp Ile
                20                  25                  30 acg gat ttt gag ttt cct caa gag att ctg ctg tac gtc cag cat gtg   144
Thr Asp Phe Glu Phe Pro Gln Glu Ile Leu Leu Tyr Val Gln His Val
            35                  40                  45 aaa aag gac atc aag gca gtc acc tat cat atc tct tct ctg gcg ctg   192
Lys Lys Asp Ile Lys Ala Val Thr Tyr His Ile Ser Ser Leu Ala Leu
        50                  55                  60 att att ttc agt ctt aaa gac tcc atc tcc ctg gcg aca gag gaa cgc   240
Ile Ile Phe Ser Leu Lys Asp Ser Ile Ser Leu Ala Thr Glu Glu Arg
65                  70                  75 ttg gaa cgt atc cgt tct ggt ctt ttc aaa caa gtg cag caa gct cgt   288
Leu Glu Arg Ile Arg Ser Gly Leu Phe Lys Gln Val Gln Gln Ala Arg
80                  85                  90                  95 gag tgc atg gta gac gag gag aac aag aac acg gag gag gac agt aca   336
Glu Cys Met Val Asp Glu Glu Asn Lys Asn Thr Glu Glu Asp Ser Thr
                100                 105                 110 tca caa cat cct cac tca gag ggc ttc aag gca gtc tac ctg gaa ttg   384
Ser Gln His Pro His Ser Glu Gly Phe Lys Ala Val Tyr Leu Glu Leu
            115                 120                 125 aac aag tat ttc ttc cgt atc cgt aag ttc ctg gta aat aag aaa tac   432
Asn Lys Tyr Phe Phe Arg Ile Arg Lys Phe Leu Val Asn Lys Lys Tyr
        130                 135                 140 agt ttc tgt gcc tgg aag att gtc gtg gtg gaa att cgt cgt tct ttc   480
Ser Phe Cys Ala Trp Lys Ile Val Val Val Glu Ile Arg Arg Ser Phe
    145                 150                 155 agt att ttt tac aaa ctg ctg aac atg aat taatggatcc                 520
Ser Ile Phe Tyr Lys Leu Leu Asn Met Asn
160                 165
```

FIG. 6

```
tctagaaagg aggaataaca t atg tgt aac ctg ctg aac gtt cac ctg cgt    51
                       Met Cys Asn Leu Leu Asn Val His Leu Arg
                        1               5               10 cgt gtt acc tgg caa aat ctg aga cat ctg agt agt atg agc aat tca    99
Arg Val Thr Trp Gln Asn Leu Arg His Leu Ser Ser Met Ser Asn Ser
            15                  20                  25 ttt cct gta gaa tgt cta cga gaa aac ata gct ttt gag ttg ccc caa   147
Phe Pro Val Glu Cys Leu Arg Glu Asn Ile Ala Phe Glu Leu Pro Gln
                30                  35                  40 gag ttt ctg caa tac acc caa cct atg aag agg gac atc aag aag gcc   195
Glu Phe Leu Gln Tyr Thr Gln Pro Met Lys Arg Asp Ile Lys Lys Ala
            45                  50                  55 ttc tat gaa atg tcc cta cag gcc ttc aac atc ttc agc caa cac acc   243
Phe Tyr Glu Met Ser Leu Gln Ala Phe Asn Ile Phe Ser Gln His Thr
        60                  65                  70 ttc aaa tat tgg aaa gag aga cac ctc aaa caa atc caa ata gga ctt   291
Phe Lys Tyr Trp Lys Glu Arg His Leu Lys Gln Ile Gln Ile Gly Leu
 75              80                  85                  90 gat cag caa gca gag tac ctg aac caa tgc ttg gag gaa gac gag aat   339
Asp Gln Gln Ala Glu Tyr Leu Asn Gln Cys Leu Glu Glu Asp Glu Asn
                95                  100                 105 gaa aat gaa gac atg aaa gaa atg aaa gag aat gag atg aaa ccc tca   387
Glu Asn Glu Asp Met Lys Glu Met Lys Glu Asn Glu Met Lys Pro Ser
            110                 115                 120 gaa gcc agg gtc ccc cag ctg agc agc ctg gaa ctg agg aga tat ttc   435
Glu Ala Arg Val Pro Gln Leu Ser Ser Leu Glu Leu Arg Arg Tyr Phe
            125                 130                 135 cac agg ata gac aat ttc ctg aaa gaa aag aaa tac agt gac tgt gcc   483
His Arg Ile Asp Asn Phe Leu Lys Glu Lys Lys Tyr Ser Asp Cys Ala
        140                 145                 150 tgg gag att gtc cga gtg gaa atc cgt cgt tgc ctg tac tac ttt tac   531
Trp Glu Ile Val Arg Val Glu Ile Arg Arg Cys Leu Tyr Tyr Phe Tyr
155                 160                 165                 170 aaa ttt acc gct ctg ttc cgt cgt aaa taatggatcc                    568
Lys Phe Thr Ala Leu Phe Arg Arg Lys
                175
```

FIG. 7

| | | | | |
|---|---|---|---|---|
| tctagaaagg aggaataaca t | atg tgt aac ctg ctg aac gtt cac ctg cgt<br>Met Cys Asn Leu Leu Asn Val His Leu Arg<br>1                               5                             10 | | | 51 |

```
          tctagaaagg aggaataaca t atg tgt aac ctg ctg aac gtt cac ctg cgt    51
                                 Met Cys Asn Leu Leu Asn Val His Leu Arg
                                  1                   5                10 cgt gtt acc tgg caa aat ctg aga cat ctg agt agt atg agc aat tca              99
Arg Val Thr Trp Gln Asn Leu Arg His Leu Ser Ser Met Ser Asn Ser
                 15                  20                  25 ttt cct gta gaa tgt cta cga gaa aac ata gct ttt gag ttg ccc caa             147
Phe Pro Val Glu Cys Leu Arg Glu Asn Ile Ala Phe Glu Leu Pro Gln
             30                  35                  40 gag ttc ctg caa tac acc caa cct atg aag agg gac atc aag aag gcc             195
Glu Phe Leu Gln Tyr Thr Gln Pro Met Lys Arg Asp Ile Lys Lys Ala
         45                  50                  55 ttc tat gaa atg tcc cta cag gcc ttc aac atc ttc agc caa cac acc             243
Phe Tyr Glu Met Ser Leu Gln Ala Phe Asn Ile Phe Ser Gln His Thr
     60                  65                  70 ttc aaa tat tgg aaa gag aga cac ctc aaa caa atc caa ata gga ctt             291
Phe Lys Tyr Trp Lys Glu Arg His Leu Lys Gln Ile Gln Ile Gly Leu
 75                  80                  85                  90 gat cag caa gca gag tac ctg aac caa tgc ttg gag gaa gac gag aat             339
Asp Gln Gln Ala Glu Tyr Leu Asn Gln Cys Leu Glu Glu Asp Glu Asn
                 95                 100                 105 gaa aat gaa gac atg aaa gaa atg aaa gag aat gag atg aaa ccc tca             387
Glu Asn Glu Asp Met Lys Glu Met Lys Glu Asn Glu Met Lys Pro Ser
             110                 115                 120 gaa gcc agg gtc ccc cag ctg agc agc ctg gaa ctg agg aga tat ttc             435
Glu Ala Arg Val Pro Gln Leu Ser Ser Leu Glu Leu Arg Arg Tyr Phe
         125                 130                 135 cac agg ata gac aat ttc ctg aaa gaa aag aaa tac agt gac tgt gcc             483
His Arg Ile Asp Asn Phe Leu Lys Glu Lys Lys Tyr Ser Asp Cys Ala
     140                 145                 150 tgg gag att gtc cga gtg gaa atc cgt cgt tct ctg tac tac ttt tac             531
Trp Glu Ile Val Arg Val Glu Ile Arg Arg Ser Leu Tyr Tyr Phe Tyr
155                 160                 165                 170 aaa ttt acc gct ctg ttc cgt cgt aaa taatggatcc                              568
Lys Phe Thr Ala Leu Phe Arg Arg Lys
                175
```

FIG. 8

```
cat atg ctg gac tgt aac ctg ctg aac gtt cac ctg cgt cgt gtt acc    48
His Met Leu Asp Cys Asn Leu Leu Asn Val His Leu Arg Arg Val Thr
 1               5                  10                  15 tgg caa aat ctg aga cat ctg agt agt atg agc aat tca ttt cct gta    96
Trp Gln Asn Leu Arg His Leu Ser Ser Met Ser Asn Ser Phe Pro Val
            20                  25                  30 gaa tgt cta cga gaa aac ata gct ttt gag ttg ccc caa gag ttt ctg   144
Glu Cys Leu Arg Glu Asn Ile Ala Phe Glu Leu Pro Gln Glu Phe Leu
                35                  40                  45 caa tac acc caa cct atg aag agg gac atc aag aag gcc ttc tat gaa   192
Gln Tyr Thr Gln Pro Met Lys Arg Asp Ile Lys Lys Ala Phe Tyr Glu
        50                  55                  60 atg tcc cta cag gcc ttc aac atc ttc agc caa cac acc ttc aaa tat   240
Met Ser Leu Gln Ala Phe Asn Ile Phe Ser Gln His Thr Phe Lys Tyr
 65                  70                  75                  80 tgg aaa gag aga cac ctc aaa caa atc caa ata gga ctt gat cag caa   288
Trp Lys Glu Arg His Leu Lys Gln Ile Gln Ile Gly Leu Asp Gln Gln
                85                  90                  95 gca gag tac ctg aac caa tgc ttg gag gaa gac gag aat gaa aat gaa   336
Ala Glu Tyr Leu Asn Gln Cys Leu Glu Glu Asp Glu Asn Glu Asn Glu
            100                 105                 110 gac atg aaa gaa atg aaa gag aat gag atg aaa ccc tca gaa gcc agg   384
Asp Met Lys Glu Met Lys Glu Asn Glu Met Lys Pro Ser Glu Ala Arg
                115                 120                 125 gtc ccc cag ctg agc agc ctg gaa ctg agg aga tat ttc cac agg ata   432
Val Pro Gln Leu Ser Ser Leu Glu Leu Arg Arg Tyr Phe His Arg Ile
        130                 135                 140 gac aat ttc ctg aaa gaa aag aaa tac agt gac tgt gcc tgg gag att   480
Asp Asn Phe Leu Lys Glu Lys Lys Tyr Ser Asp Cys Ala Trp Glu Ile
145                 150                 155                 160 gtc cga gtg gaa atc cgt cgt tgc ctg tac tac ttt tac aaa ttt acc   528
Val Arg Val Glu Ile Arg Arg Cys Leu Tyr Tyr Phe Tyr Lys Phe Thr
                165                 170                 175 gct ctg ttc cgt cgt aaa taatggatcc                                 556
Ala Leu Phe Arg Arg Lys
                180
```

INTERFERON-LIKE MOLECULES AND USES THEREOF

This application is a continuation of U.S. application Ser. No. 09/724,860, filed on Nov. 8, 2000 now abandoned, which claims the benefit of U.S. Provisional Application No. 60/169,720, filed on Dec. 8, 1999, the disclosure of each of which is explicitly incorporated by reference herein.

FIELD OF THE INVENTION

The present invention relates to Interferon-Like (IFN-L) polypeptides and nucleic acid molecules encoding the same. The invention also relates to selective binding agents, vectors, host cells, and methods for producing IFN-L polypeptides. The invention further relates to pharmaceutical compositions and methods for the diagnosis, treatment, amelioration, and/or prevention of diseases, disorders, and conditions associated with IFN-L polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified.

Accordingly, it is an object of the invention to identify novel polypeptides, and nucleic acid molecules encoding the same, which have diagnostic or therapeutic benefit.

SUMMARY OF THE INVENTION

The present invention relates to novel IFN-L nucleic acid molecules and encoded polypeptides.

The invention provides for an isolated nucleic acid molecule comprising a nucleotide sequence selected from the group consisting of:
  (a) the nucleotide sequence as set forth in either SEQ ID NO: 1 or SEQ ID NO: 4;
  (b) the nucleotide sequence of the DNA insert in ATCC Deposit No. PTA-976;
  (c) a nucleotide sequence encoding the polypeptide as set forth in either SEQ ID NO: 2 or SEQ ID NO: 5;
  (d) a nucleotide sequence which hybridizes under moderately or highly stringent conditions to the complement of any of (a)-(c); and
  (e) a nucleotide sequence complementary to any of (a)-(c).

The invention also provides for an isolated nucleic acid molecule comprising a nucleotide sequence selected from the group consisting of:
  (a) a nucleotide sequence encoding a polypeptide which is at least about 70 percent identical to the polypeptide as set forth in either SEQ ID NO: 2 or SEQ ID NO: 5, wherein the encoded polypeptide has an activity of the polypeptide set forth in either SEQ ID NO: 2 or SEQ ID NO: 5;
  (b) a nucleotide sequence encoding an allelic variant or splice variant of the nucleotide sequence as set forth in either SEQ ID NO: 1 or SEQ ID NO: 4, the nucleotide sequence of the DNA insert in ATCC Deposit No. PTA-976, or (a);
  (c) a region of the nucleotide sequence of either SEQ ID NO: 1 or SEQ ID NO: 4, the DNA insert in ATCC Deposit No. PTA-976, (a), or (b) encoding a polypeptide fragment of at least about 25 amino acid residues, wherein the polypeptide fragment has an activity of the encoded polypeptide as set forth in either SEQ ID NO: 2 or SEQ ID NO: 5, or is antigenic;
  (d) a region of the nucleotide sequence of either SEQ ID NO: 1 or SEQ ID NO: 4, the DNA insert in ATCC Deposit No. PTA-976, or any of (a)-(c) comprising a fragment of at least about 16 nucleotides;
  (e) a nucleotide sequence which hybridizes under moderately or highly stringent conditions to the complement of any of (a)-(d); and
  (f) a nucleotide sequence complementary to any of (a)-(d).

The invention further provides for an isolated nucleic acid molecule comprising a nucleotide sequence selected from the group consisting of:
  (a) a nucleotide sequence encoding a polypeptide as set forth in either SEQ ID NO: 2 or SEQ ID NO: 5 with at least one conservative amino acid substitution, wherein the encoded polypeptide has an activity of the polypeptide set forth in either SEQ ID NO: 2 or SEQ ID NO: 5;
  (b) a nucleotide sequence encoding a polypeptide as set forth in either SEQ ID NO: 2 or SEQ ID NO: 5 with at least one amino acid insertion, wherein the encoded polypeptide has an activity of the polypeptide set forth in either SEQ ID NO: 2 or SEQ ID NO: 5;
  (c) a nucleotide sequence encoding a polypeptide as set forth in either SEQ ID NO: 2 or SEQ ID NO: 5 with at least one amino acid deletion, wherein the encoded polypeptide has an activity of the polypeptide set forth in either SEQ ID NO: 2 or SEQ ID NO: 5;
  (d) a nucleotide sequence encoding a polypeptide as set forth in either SEQ ID NO: 2 or SEQ ID NO: 5 which has a C- and/or N-terminal truncation, wherein the encoded polypeptide has an activity of the polypeptide set forth in either SEQ ID NO: 2 or SEQ ID NO: 5;
  (e) a nucleotide sequence encoding a polypeptide as set forth in either SEQ ID NO: 2 or SEQ ID NO: 5 with at least one modification selected from the group consisting of amino acid substitutions, amino acid insertions, amino acid deletions, C-terminal truncation, and N-terminal truncation, wherein the encoded polypeptide has an activity of the polypeptide set forth in either SEQ ID NO: 2 or SEQ ID NO: 5;
  (f) a nucleotide sequence of any of (a)-(e) comprising a fragment of at least about 16 nucleotides;
  (g) a nucleotide sequence which hybridizes under moderately or highly stringent conditions to the complement of any of (a)-(f); and
  (h) a nucleotide sequence complementary to any of (a)-(e).

The present invention provides for an isolated polypeptide comprising an amino acid sequence selected from the group consisting of:
  (a) the amino acid sequence as set forth in either SEQ ID NO: 2 or SEQ ID NO: 5; and
  (b) the amino acid sequence encoded by the DNA insert in ATCC Deposit No. PTA-976.

The invention also provides for an isolated polypeptide comprising the amino acid sequence selected from the group consisting of:
  (a) the amino acid sequence as set forth in either SEQ ID NO: 3 or SEQ ID NO: 6, optionally further comprising an amino-terminal methionine;
  (b) an amino acid sequence for an ortholog of either SEQ ID NO: 2 or SEQ ID NO: 5;
  (c) an amino acid sequence which is at least about 70 percent identical to the amino acid sequence of either SEQ ID NO: 2 or SEQ ID NO: 5, wherein the polypeptide has an activity of the polypeptide set forth in either SEQ ID NO: 2 or SEQ ID NO: 5;
  (d) a fragment of the amino acid sequence set forth in either SEQ ID NO: 2 or SEQ ID NO: 5 comprising at least about 25 amino acid residues, wherein the fragment has an activity of the polypeptide set forth in either SEQ ID NO: 2 or SEQ ID NO: 5, or is antigenic; and
  (e) an amino acid sequence for an allelic variant or splice variant of the amino acid sequence as set forth in either SEQ ID NO: 2 or SEQ ID NO: 5, the amino acid sequence encoded by the DNA insert in ATCC Deposit No. PTA-976, or any of (a)-(c).

The invention further provides for an isolated polypeptide comprising the amino acid sequence selected from the group consisting of:
  (a) the amino acid sequence as set forth in either SEQ ID NO: 2 or SEQ ID NO: 5 with at least one conservative amino acid substitution, wherein the polypeptide has an activity of the polypeptide set forth in either SEQ ID NO: 2 or SEQ ID NO: 5;
  (b) the amino acid sequence as set forth in either SEQ ID NO: 2 or SEQ ID NO: 5 with at least one amino acid insertion, wherein the polypeptide has an activity of the polypeptide set forth in either SEQ ID NO: 2 or SEQ ID NO: 5;
  (c) the amino acid sequence as set forth in either SEQ ID NO: 2 or SEQ ID NO: 5 with at least one amino acid deletion, wherein the polypeptide has an activity of the polypeptide set forth in either SEQ ID NO: 2 or SEQ ID NO: 5;
  (d) the amino acid sequence as set forth in either SEQ ID NO: 2 or SEQ ID NO: 5 which has a C- and/or N-terminal truncation, wherein the polypeptide has an activity of the polypeptide set forth in either SEQ ID NO: 2 or SEQ ID NO: 5; and
  (e) the amino acid sequence as set forth in either SEQ ID NO: 2 or SEQ ID NO: 5 with at least one modification selected from the group consisting of amino acid substitutions, amino acid insertions, amino acid deletions, C-terminal truncation, and N-terminal truncation, wherein the polypeptide has an activity of the polypeptide set forth in either SEQ ID NO: 2 or SEQ ID NO: 5.

Also provided are fusion polypeptides comprising IFN-L amino acid sequences.

The present invention also provides for an expression vector comprising the isolated nucleic acid molecules as set forth herein, recombinant host cells comprising the recombinant nucleic acid molecules as set forth herein, and a method of producing an IFN-L polypeptide comprising culturing the host cells and optionally isolating the polypeptide so produced.

A transgenic non-human animal comprising a nucleic acid molecule encoding an IFN-L polypeptide is also encompassed by the invention. The IFN-L nucleic acid molecules are introduced into the animal in a manner that allows expression and increased levels of an IFN-L polypeptide, which may include increased circulating levels. Alternatively, the IFN-L nucleic acid molecules are introduced into the animal in a manner that prevents expression of endogenous IFN-L polypeptide (i.e., generates a transgenic animal possessing an IFN-L polypeptide gene knockout). The transgenic non-human animal is preferably a mammal, and more preferably a rodent, such as a rat or a mouse.

Also provided are derivatives of the IFN-L polypeptides of the present invention.

Additionally provided are selective binding agents such as antibodies and peptides capable of specifically binding the IFN-L polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The IFN-L polypeptides and nucleic acid molecules of the present invention may be used to treat, prevent, ameliorate, and/or detect diseases and disorders, including those recited herein.

The present invention also provides a method of assaying test molecules to identify a test molecule that binds to an IFN-L polypeptide. The method comprises contacting an IFN-L polypeptide with a test molecule to determine the extent of binding of the test molecule to the polypeptide. The method further comprises determining whether such test molecules are agonists or antagonists of an IFN-L polypeptide. The present invention further provides a method of testing the impact of molecules on the expression of IFN-L polypeptide or on the activity of IFN-L polypeptide.

Methods of regulating expression and modulating (i.e., increasing or decreasing) levels of an IFN-L polypeptide are also encompassed by the invention. One method comprises administering to an animal a nucleic acid molecule encoding an IFN-L polypeptide. In another method, a nucleic acid molecule comprising elements that regulate or modulate the expression of an IFN-L polypeptide may be administered. Examples of these methods include gene therapy, cell therapy, and anti-sense therapy as further described herein.

In another aspect of the present invention, the IFN-L polypeptides may be used for identifying receptors thereof ("IFN-L polypeptide receptors"). Various forms of "expression cloning" have been extensively used to clone receptors for protein ligands. See, e.g., Simonsen and Lodish, 1994, *Trends Pharmacol. Sci.* 15:437-41 and Tartaglia et al., 1995, *Cell* 83:1263-71. The isolation of an IFN-L polypeptide receptor is useful for identifying or developing novel agonists and antagonists of the IFN-L polypeptide signaling pathway. Such agonists and antagonists include soluble IFN-L polypeptide receptors, anti-IFN-L polypeptide receptor-selective binding agents (such as antibodies and derivatives thereof), small molecules, and antisense oligonucleotides, any of which can be used for treating one or more disease or disorder, including those disclosed herein.

BRIEF DESCRIPTION OF THE FIGURES

FIGS. 1A-1B illustrate the nucleotide sequence of the rat IFN-L gene (SEQ ID NO: 1) and the deduced amino acid sequence of rat IFN-L polypeptide (SEQ ID NO: 2). The predicted signal peptide is indicated (underlined);

FIGS. 2A-2B illustrate the nucleotide sequence of the human IFN-L gene (SEQ ID NO: 4) and the deduced amino acid sequence of human IFN-L polypeptide (SEQ ID NO: 5). The predicted signal peptide is indicated (underlined);

FIG. 3 illustrates the amino acid sequence alignment of human IFN-L polypeptide (huIFN-L; SEQ ID NO: 5), human IFN-β (huIFN-β; SEQ ID NO: 7), rat IFN-L polypeptide (raIFN-L; SEQ ID NO: 2), and those amino acid positions which share some similarity (cons);

FIG. 4 illustrates the nucleotide sequence of the Nde I-Bam HI pAMG21 insert (SEQ ID NO: 8) of Amgen strain #3729 and the predicted amino acid sequence (SEQ ID NO: 9) encoded by this insert;

FIG. 5 illustrates the nucleotide sequence of the Nde I-Bam HI pAMG21 insert (SEQ ID NO: 10) of Amgen strain #3858 and the predicted amino acid sequence (SEQ ID NO: 11) encoded by this insert;

FIG. 6 illustrates the nucleotide sequence of the Xba I-Bam HI pAMG21 insert (SEQ ID NO: 12) of Amgen strain #4047 and the predicted amino acid sequence (SEQ ID NO: 13) encoded by this insert;

FIG. 7 illustrates the nucleotide sequence of the Xba I-Bam HI pAMG21 insert (SEQ ID NO: 14) of Amgen strain #3969 and the predicted amino acid sequence (SEQ ID NO: 15) encoded by this insert;

FIG. 8 illustrates the nucleotide sequence of the Nde I-Bam HI pAMG21 insert (SEQ ID NO: 16) of Amgen strain #4182 and the predicted amino acid sequence (SEQ ID NO: 17) encoded by this insert.

DETAILED DESCRIPTION OF THE INVENTION

The section headings used herein are for organizational purposes only and are not to be construed as limiting the subject matter described. All references cited in this application are expressly incorporated by reference herein.

DEFINITIONS

The terms "IFN-L gene" or "IFN-L nucleic acid molecule" or "IFN-L polynucleotide" refer to a nucleic acid molecule comprising or consisting of a nucleotide sequence as set forth in either SEQ ID NO: 1 or SEQ ID NO: 4, a nucleotide sequence encoding the polypeptide as set forth in either SEQ ID NO: 2 or SEQ ID NO: 5, a nucleotide sequence of the DNA insert in ATCC Deposit No. PTA-976, and nucleic acid molecules as defined herein.

The term "IFN-L polypeptide allelic variant" refers to one of several possible naturally occurring alternate forms of a gene occupying a given locus on a chromosome of an organism or a population of organisms.

The term "IFN-L polypeptide splice variant" refers to a nucleic acid molecule, usually RNA, which is generated by alternative processing of intron sequences in an RNA transcript of IFN-L polypeptide amino acid sequence as set forth in either SEQ ID NO: 2 or SEQ ID NO: 5.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g., nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is not limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "IFN-L polypeptide" refers to a polypeptide comprising the amino acid sequence of either SEQ ID NO: 2 or SEQ ID NO: 5 and related polypeptides. Related polypeptides include IFN-L polypeptide fragments, IFN-L polypeptide orthologs, IFN-L polypeptide variants, and IFN-L polypeptide derivatives, which possess at least one activity of the polypeptide as set forth in either SEQ ID NO: 2 or SEQ ID NO: 5. IFN-L polypeptides may be mature polypeptides, as defined herein, and may or may not have an amino-terminal methionine residue, depending on the method by which they are prepared.

The term "IFN-L polypeptide fragment" refers to a polypeptide that comprises a truncation at the amino-terminus (with or without a leader sequence) and/or a truncation at the carboxyl-terminus of the polypeptide as set forth in either SEQ ID NO: 2 or SEQ ID NO: 5. The term "IFN-L polypeptide fragment" also refers to amino-terminal and/or carboxyl-terminal truncations of IFN-L polypeptide orthologs, IFN-L polypeptide derivatives, or IFN-L polypeptide variants, or to amino-terminal and/or carboxyl-terminal truncations of the polypeptides encoded by IFN-L polypeptide allelic variants or IFN-L polypeptide splice variants. IFN-L polypeptide fragments may result from alternative RNA splicing or from in vivo protease activity. Membrane-bound forms of an IFN-L polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such IFN-L polypeptide fragments may optionally comprise an amino-terminal methionine residue. It will be appreciated that such fragments can be used, for example, to generate antibodies to IFN-L polypeptides.

The term "IFN-L polypeptide ortholog" refers to a polypeptide from another species that corresponds to IFN-L polypeptide amino acid sequence as set forth in either SEQ ID NO: 2 or SEQ ID NO: 5. For example, mouse and human IFN-L polypeptides are considered orthologs of each other.

The term "IFN-L polypeptide variants" refers to IFN-L polypeptides comprising amino acid sequences having one or more amino acid sequence substitutions, deletions (such as internal deletions and/or IFN-L polypeptide fragments), and/or additions (such as internal additions and/or IFN-L fusion polypeptides) as compared to the IFN-L polypeptide amino acid sequence set forth in either SEQ ID NO: 2 or SEQ ID NO: 5 (with or without a leader sequence). Variants may be naturally occurring (e.g., IFN-L polypeptide allelic variants, IFN-L polypeptide orthologs, and IFN-L polypeptide splice variants) or artificially constructed. Such IFN-L polypeptide variants may be prepared from the corresponding nucleic acid molecules having a DNA sequence that varies accordingly from the DNA sequence as set forth in either SEQ ID NO: 1 or SEQ ID NO: 4. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "IFN-L polypeptide derivatives" refers to the polypeptide as set forth in either SEQ ID NO: 2 or SEQ ID NO: 5, IFN-L polypeptide fragments, IFN-L polypeptide orthologs, or IFN-L polypeptide variants, as defined herein, that have been chemically modified. The term "IFN-L polypeptide derivatives" also refers to the polypeptides encoded by IFN-L polypeptide allelic variants or IFN-L polypeptide splice variants, as defined herein, that have been chemically modified.

The term "mature IFN-L polypeptide" refers to an IFN-L polypeptide lacking a leader sequence. A mature IFN-L polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like. Exemplary mature IFN-L polypeptides are depicted by the amino acid sequences of SEQ ID NO: 3 and SEQ ID NO: 6.

The term "IFN-L fusion polypeptide" refers to a fusion of one or more amino acids (such as a heterologous protein or peptide) at the amino- or carboxyl-terminus of the polypeptide as set forth in either SEQ ID NO: 2 or SEQ ID NO: 5, IFN-L polypeptide fragments, IFN-L polypeptide orthologs, IFN-L polypeptide variants, or IFN-L derivatives, as defined herein. The term "IFN-L fusion polypeptide" also refers to a fusion of one or more amino acids at the amino- or carboxyl-terminus of the polypeptide encoded by IFN-L polypeptide allelic variants or IFN-L polypeptide splice variants, as defined herein.

The term "biologically active IFN-L polypeptides" refers to IFN-L polypeptides having at least one activity characteristic of the polypeptide comprising the amino acid sequence of either SEQ ID NO: 2 or SEQ ID NO: 5. In addition, an IFN-L polypeptide may be active as an immunogen; that is, the IFN-L polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness which includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The terms "effective amount" and "therapeutically effective amount" each refer to the amount of an IFN-L polypeptide or IFN-L nucleic acid molecule used to support an observable level of one or more biological activities of the IFN-L polypeptides as set forth herein.

The term "pharmaceutically acceptable carrier" or "physiologically acceptable carrier" as used herein refers to one or more formulation materials suitable for accomplishing or enhancing the delivery of the IFN-L polypeptide, IFN-L nucleic acid molecule, or IFN-L selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for an IFN-L polypeptide. As used herein, the terms, "specific" and "specificity" refer to the ability of the selective binding agents to bind to human IFN-L polypeptides and not to bind to human non-IFN-L polypeptides. It will be appreciated, however, that the selective binding agents may also bind orthologs of the polypeptide as set forth in either SEQ ID NO: 2 or SEQ ID NO: 5, that is, interspecies versions thereof, such as mouse and rat IFN-L polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of either SEQ ID NO: 1 or SEQ ID NO: 4, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide in either SEQ ID NO: 2 or SEQ ID NO: 5. Such related IFN-L polypeptides may comprise, for example, an addition and/or a deletion of one or more N-linked or O-linked glycosylation sites or an addition and/or a deletion of one or more cysteine residues.

Related nucleic acid molecules also include fragments of IFN-L nucleic acid molecules which encode a polypeptide of at least about 25 contiguous amino acids, or about 50 amino acids, or about 75 amino acids, or about 100 amino acids, or about 150 amino acids, or about 200 amino acids, or more than 200 amino acid residues of the IFN-L polypeptide of either SEQ ID NO: 2 or SEQ ID NO:5.

In addition, related IFN-L nucleic acid molecules also include those molecules which comprise nucleotide sequences which hybridize under moderately or highly stringent conditions as defined herein with the fully complementary sequence of the IFN-L nucleic acid molecule of either SEQ ID NO: 1 or SEQ ID NO: 4, or of a molecule encoding a polypeptide, which polypeptide comprises the amino acid sequence as shown in either SEQ ID NO: 2 or SEQ ID NO: 5, or of a nucleic acid fragment as defined herein, or of a nucleic acid fragment encoding a polypeptide as defined herein. Hybridization probes may be prepared using the IFN-L sequences provided herein to screen cDNA, genomic or synthetic DNA libraries for related sequences. Regions of the DNA and/or amino acid sequence of IFN-L polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, $NaDodSO_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(°C.)=81.5+16.6(\log [Na+])+0.41(\% G+C)-600/N-0.72(\% \text{formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm=2° C. \text{ per A-T base pair}+4° C. \text{ per G-C base pair}$$

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is at least about 70 percent identical to the nucleotide sequence as shown in either SEQ ID NO: 1 or SEQ ID NO: 4, or comprise or consist essentially of a nucleotide sequence encoding a polypeptide that is at least about 70 percent identical to the polypeptide as set forth in either SEQ ID NO: 2 or SEQ ID NO: 5. In preferred embodiments, the nucleotide sequences are about 75 percent, or about 80 percent, or about 85 percent, or about 90 percent, or about 95, 96, 97, 98, or 99 percent identical to the nucleotide sequence as shown in either SEQ ID NO: 1 or SEQ ID NO: 4, or the nucleotide sequences encode a polypeptide that is about 75 percent, or about 80 percent, or about 85 percent, or about 90 percent, or about 95, 96, 97, 98, or 99 percent identical to the polypeptide sequence as set forth in either SEQ ID NO: 2 or SEQ ID NO: 5. Related nucleic acid molecules encode polypeptides possessing at least one activity of the polypeptide set forth in either SEQ ID NO: 2 or SEQ ID NO: 5.

Differences in the nucleic acid sequence may result in conservative and/or non-conservative modifications of the amino acid sequence relative to the amino acid sequence of either SEQ ID NO: 2 or SEQ ID NO: 5.

Conservative modifications to the amino acid sequence of either SEQ ID NO: 2 or SEQ ID NO: 5 (and the corresponding modifications to the encoding nucleotides) will produce a polypeptide having functional and chemical characteristics similar to those of IFN-L polypeptides. In contrast, substantial modifications in the functional and/or chemical characteristics of IFN-L polypeptides may be accomplished by selecting substitutions in the amino acid sequence of either SEQ ID NO: 2 or SEQ ID NO: 5 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human IFN-L polypeptide that are homologous with non-human IFN-L polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the IFN-L polypeptide, or to increase or decrease the affinity of the IFN-L polypeptides described herein. Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in either SEQ ID NO: 2 or SEQ ID NO: 5 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of an IFN-L polypeptide to such similar polypeptides. With such a comparison, one can identify residues and portions of the molecules that are conserved among similar polypeptides. It will be appreciated that changes in areas of the IFN-L molecule that are not conserved relative to such similar polypeptides would be less likely to adversely affect the biological activity and/or structure of an IFN-L polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an IFN-L polypeptide that correspond to amino acid residues that are important for activity or structure in similar polypeptides. One skilled in the art may opt for chemically similar amino acid substitutions for such predicted important amino acid residues of IFN-L polypeptides.

One skilled in the art can also analyze the three-dimensional structure and amino acid sequence in relation to that structure in similar polypeptides. In view of such information, one skilled in the art may predict the alignment of amino acid residues of IFN-L polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol. Relat. Areas Mol. Biol.* 47:45-48; Chou et al., 1978, *Ann. Rev. Biochem.* 47:251-276; and Chou et al., 1979, *Biophys. J* 26:367-84. Moreover, computer programs are currently available to assist with predicting secondary structure. One method of predicting secondary structure is based upon homology modeling. For example, two polypeptides or proteins which have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244-47.

It has been suggested that there are a limited number of folds in a given polypeptide or protein and that once a critical number of structures have been resolved, structural prediction will become dramatically more accurate (Brenner et al., 1997, *Curr. Opin. Struct. Biol.* 1:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science*, 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred IFN-L polypeptide variants include glycosylation variants wherein the number and/or type of glycosylation sites have been altered compared to the amino acid sequence set forth in either SEQ ID NO: 2 or SEQ ID NO: 5. In one embodiment, IFN-L polypeptide variants comprise a greater or a lesser number of N-linked glycosylation sites than the amino acid sequence set forth in either SEQ ID NO: 2 or SEQ ID NO: 5. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred IFN-L variants include cysteine variants, wherein one or more cysteine residues are deleted or substituted with another amino acid (e.g., serine) as compared to the amino acid sequence set forth in either SEQ ID NO: 2 or SEQ ID NO: 5. Cysteine variants are useful when IFN-L polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, related nucleic acid molecules comprise or consist of a nucleotide sequence encoding a polypeptide as set forth in either SEQ ID NO: 2 or SEQ ID NO: 5 with at least one amino acid insertion and wherein the polypeptide has an activity of the polypeptide set forth in either SEQ ID NO: 2 or SEQ ID NO: 5, or a nucleotide sequence encoding a polypeptide as set forth in either SEQ ID NO: 2 or SEQ ID NO: 5 with at least one amino acid deletion and wherein the polypeptide has an activity of the polypeptide set forth in either SEQ ID NO: 2 or SEQ ID NO: 5. Related nucleic acid molecules also comprise or consist of a nucleotide sequence encoding a polypeptide as set forth in either SEQ ID NO: 2 or SEQ ID NO: 5 wherein the polypeptide has a carboxyl- and/or amino-terminal truncation and further wherein the polypeptide has an activity of the polypeptide set forth in either SEQ ID NO: 2 or SEQ ID NO: 5. Related nucleic acid molecules also comprise or consist of a nucleotide sequence encoding a polypeptide as set forth in either SEQ ID NO: 2 or SEQ ID NO: 5 with at least one modification selected from the group consisting of amino acid substitutions, amino acid insertions, amino acid deletions, carboxyl-terminal truncations, and amino-terminal truncations and wherein the polypeptide has an activity of the polypeptide set forth in either SEQ ID NO: 2 or SEQ ID NO: 5.

In addition, the polypeptide comprising the amino acid sequence of either SEQ ID NO: 2 or SEQ ID NO: 5, or other IFN-L polypeptide, may be fused to a homologous polypeptide to form a homodimer or to a heterologous polypeptide to form a heterodimer. Heterologous peptides and polypeptides include, but are not limited to: an epitope to allow for the detection and/or isolation of an IFN-L fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in either SEQ ID NO: 2 or SEQ ID NO: 5, or other IFN-L polypeptide.

Fusions can be made either at the amino-terminus or at the carboxyl-terminus of the polypeptide comprising the amino acid sequence set forth in either SEQ ID NO: 2 or SEQ ID NO: 5, or other IFN-L polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of either SEQ ID NO: 2 or SEQ ID NO: 5, or other IFN-L polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, *Nature* 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

TABLE II

| Fc Fusion with Therapeutic Proteins | | | |
|---|---|---|---|
| Form of Fc | Fusion partner | Therapeutic implications | Reference |
| IgG1 | N-terminus of CD30-L | Hodgkin's disease; anaplastic lymphoma; T-cell leukemia | U.S. Pat. No. 5,480,981 |

TABLE II-continued

Fc Fusion with Therapeutic Proteins

| Form of Fc | Fusion partner | Therapeutic implications | Reference |
|---|---|---|---|
| Murine Fcγ2a | IL-10 | anti-inflammatory; transplant rejection | Zheng et al., 1995, J. Immunol. 154: 5590-600 |
| IgG1 | TNF receptor | septic shock | Fisher et al., 1996, N. Engl. J. Med. 334: 1697-1702; Van Zee et al., 1996, J. Immunol. 156: 2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, Nature 337: 525-31 |
| IgG1, IgG3 | N-terminus of IL-2 | anti-cancer, antiviral | Harvill et al., 1995, Immunotech. 1: 95-105 |
| IgG1 | C-terminus of OPG | osteoarthritis; bone density | WO 97/23614 |
| IgG1 | N-terminus of leptin | anti-obesity | PCT/US 97/23183, filed Dec. 11, 1997 |
| Human Ig Cγ1 | CTLA-4 | autoimmune disorders | Linsley, 1991, J. Exp. Med., 174: 561-69 |

In one example, a human IgG hinge, CH2, and CH3 region may be fused at either the amino-terminus or carboxyl-terminus of the IFN-L polypeptides using methods known to the skilled artisan. In another example, a human IgG hinge, CH2, and CH3 region may be fused at either the amino-terminus or carboxyl-terminus of an IFN-L polypeptide fragment (e.g., the predicted extracellular portion of IFN-L polypeptide).

The resulting IFN-L fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM J. Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978)(PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:

Algorithm: Needleman and Wunsch, 1970, *J. Mol. Biol.* 48:443-53;
Comparison matrix: BLOSUM 62 (Henikoff et al., supra);
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman and Wunsch, supra;
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of an IFN-L polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of an IFN-L polypeptide has been identified from one species, all or a portion of that gene may be used as a probe to identify orthologs or related genes from the same species. The probes or primers may be used to screen cDNA libraries from various tissue sources believed to express the IFN-L polypeptide. In addition, part or all of a nucleic acid molecule having the sequence as set forth in either SEQ ID NO: 1 or SEQ ID NO: 4 may be used to screen a genomic library to identify and isolate a gene encoding the amino acid sequence of an IFN-L polypeptide. Typically, conditions of moderate or high stringency will be employed for screening to minimize the number of false positives obtained from the screening.

Nucleic acid molecules encoding the amino acid sequence of IFN-L polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of an IFN-L polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of an IFN-L polypeptide can be inserted into an expression vector. By introducing the expression vector into an appropriate host, the encoded IFN-L polypeptide may be produced in large amounts.

Another method for obtaining a suitable nucleic acid sequence is the polymerase chain reaction (PCR). In this method, cDNA is prepared from poly(A)+ RNA or total RNA using the enzyme reverse transcriptase. Two primers, typically complementary to two separate regions of cDNA encoding the amino acid sequence of an IFN-L polypeptide, are then added to the cDNA along with a polymerase such as Taq polymerase, and the polymerase amplifies the cDNA region between the two primers.

Another means of preparing a nucleic acid molecule encoding the amino acid sequence of an IFN-L polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of an IFN-L polypeptide will be several hundred nucleotides in length. Nucleic acids larger than about 100 nucleotides can be synthesized as several fragments using these methods. The fragments can then be ligated together to form the full-length nucleotide sequence of an IFN-L gene. Usually, the DNA fragment encoding the amino-terminus of the polypeptide will have an ATG, which encodes a methionine residue. This methionine may or may not be present on the mature form of the IFN-L polypeptide, depending on whether the polypeptide produced in the host cell is designed to be secreted from that cell. Other methods known to the skilled artisan may be used as well.

In certain embodiments, nucleic acid variants contain codons which have been altered for optimal expression of an IFN-L polypeptide in a given host cell. Particular codon alterations will depend upon the IFN-L polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "*Drosophila*_high.cod," "Human_high.cod," "Maize_high.cod," and "Yeast_high.cod."

In some cases, it may be desirable to prepare nucleic acid molecules encoding IFN-L polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of an IFN-L polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of an IFN-L polypeptide may be amplified/expressed in prokaryotic, yeast, insect (baculovirus systems) and/or eukaryotic host cells. Selection of the host cell will depend in part on whether an IFN-L polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the IFN-L polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the IFN-L polypeptide from the host cell. Affinity purification can be accomplished, for example, by column chromatography using antibodies against the tag as an affinity matrix. Optionally, the tag can subsequently be removed from the purified IFN-L polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences which normally function to regulate IFN-L polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the IFN-L gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of an IFN-L polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes an IFN-L polypeptide. As a result, increased quantities of IFN-L polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of an IFN-L polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct an IFN-L polypeptide out of the host cell. Typically, a nucleotide sequence encoding the signal sequence is positioned in the coding region of an IFN-L nucleic acid molecule, or directly at the 5' end of an IFN-L polypeptide coding region. Many signal sequences have been identified, and any of those that are functional in the selected host cell may be used in conjunction with an IFN-L nucleic acid molecule. Therefore, a signal sequence may be homologous (naturally occurring) or heterologous to the IFN-L nucleic acid molecule. Additionally, a signal sequence may be chemically synthesized using methods described herein. In most cases, the secretion of an IFN-L polypeptide from the host cell via the presence of a signal peptide will result in the removal of the signal peptide from the secreted IFN-L polypeptide. The signal sequence may be a component of the vector, or it may be a part of an IFN-L nucleic acid molecule that is inserted into the vector.

Included within the scope of this invention is the use of either a nucleotide sequence encoding a native IFN-L polypeptide signal sequence joined to an IFN-L polypeptide coding region or a nucleotide sequence encoding a heterologous signal sequence joined to an IFN-L polypeptide coding region. The heterologous signal sequence selected should be one that is recognized and processed, i.e., cleaved by a signal peptidase, by the host cell. For prokaryotic host cells that do not recognize and process the native IFN-L polypeptide signal sequence, the signal sequence is substituted by a prokaryotic signal sequence selected, for example, from the group of the alkaline phosphatase, penicillinase, or heat-stable enterotoxin II leaders. For yeast secretion, the native IFN-L polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired IFN-L polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the IFN-L gene especially where the gene used is a full-length genomic sequence or a fragment thereof. Where the intron is not naturally occurring within the gene (as for most cDNAs), the intron may be obtained from another source. The position of the intron with respect to flanking sequences and the IFN-L gene is generally important, as the intron must be transcribed to be effective. Thus, when an IFN-L cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the IFN-L polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding IFN-L polypeptide by removing the promoter from the source DNA by restriction enzyme digestion and inserting the desired promoter sequence into the vector. The native IFN-L promoter sequence may be used to direct amplification and/or expression of an IFN-L nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling IFN-L gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-feto-protein gene control region which is active in liver (Krumlauf et al., 1985, *Mol. Cell. Biol.*, 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315: 338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234: 1372-78).

An enhancer sequence may be inserted into the vector to increase the transcription of a DNA encoding an IFN-L polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to an IFN-L nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule encoding an IFN-L polypeptide has been inserted into the proper site of the vector, the completed vector may be inserted into a suitable host cell for amplification and/or polypeptide expression. The transformation of an expression vector for an IFN-L polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes an IFN-L polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(-) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques*, 14:810-17; Lucklow, 1993, *Curr. Opin. Biotechnol.* 4:564-72; and Lucklow et al., 1993, *J. Virol.*, 67:4566-79. Preferred insect cells are Sf-9 and Hi5 (Invitrogen).

One may also use transgenic animals to express glycosylated IFN-L polypeptides. For example, one may use a transgenic milk-producing animal (a cow or goat, for example) and obtain the present glycosylated polypeptide in the animal milk. One may also use plants to produce IFN-L polypeptides, however, in general, the glycosylation occurring in plants is different from that produced in mammalian cells, and may result in a glycosylated product which is not suitable for human therapeutic use.

Polypeptide Production

Host cells comprising an IFN-L polypeptide expression vector may be cultured using standard media well known to the skilled artisan. The media will usually contain all nutrients necessary for the growth and survival of the cells.

Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of an IFN-L polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If an IFN-L polypeptide has been designed to be secreted from the host cells, the majority of polypeptide may be found in the cell culture medium. If however, the IFN-L polypeptide is not secreted from the host cells, it will be present in the cytoplasm and/or the nucleus (for eukaryotic host cells) or in the cytosol (for gram-negative bacteria host cells).

For an IFN-L polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If an IFN-L polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized IFN-L polypeptide can then be analyzed using gel electrophoresis, immunoprecipitation, or the like. If it is desired to isolate the IFN-L polypeptide, isolation may be accomplished using standard methods such as those described herein and in Marston et al., 1990, *Meth. Enz.*, 182:264-75.

In some cases, an IFN-L polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol (DTT)/dithiane DTT, and 2-2-mercaptoethanol (bME)/dithio-b(ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of an IFN-L polypeptide, then the polypeptide will be found primarily in the supernatant after centrifugation of the cell homogenate. The polypeptide may be further isolated from the supernatant using methods such as those described herein.

The purification of an IFN-L polypeptide from solution can be accomplished using a variety of techniques. If the polypeptide has been synthesized such that it contains a tag such as Hexahistidine (IFN-L polypeptide/hexaHis) or other small peptide such as FLAG (Eastman Kodak Co., New Haven, Conn.) or myc (Invitrogen, Carlsbad, Calif.) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of IFN-L polypeptide/polyHis. See, e.g., *Current Protocols in Molecular Biology* §10 Nov. 8 (Ausubel et al., eds., Green Publishers Inc. and Wiley and Sons 1993).

Additionally, IFN-L polypeptides may be purified through the use of a monoclonal antibody that is capable of specifically recognizing and binding to an IFN-L polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

IFN-L polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized IFN-L polypeptides may be oxidized using methods set forth in these references to form disulfide bridges. Chemically synthesized IFN-L polypeptides are expected to have comparable biological activity to the corresponding IFN-L polypeptides produced recombinantly or purified from natural sources, and thus may be used interchangeably with a recombinant or natural IFN-L polypeptide.

Another means of obtaining IFN-L polypeptide is via purification from biological samples such as source tissues and/or fluids in which the IFN-L polypeptide is naturally found. Such purification can be conducted using methods for protein purification as described herein. The presence of the IFN-L polypeptide during purification may be monitored, for example, using an antibody prepared against recombinantly produced IFN-L polypeptide or peptide fragments thereof.

A number of additional methods for producing nucleic acids and polypeptides are known in the art, and the methods can be used to produce polypeptides having specificity for IFN-L polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817, 483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive IFN-L polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more IFN-L polypeptides. Suitable selective binding agents include, but are not limited to, antibodies and derivatives thereof, polypeptides, and small molecules. Suitable selective binding agents may be prepared using methods known in the art. An exemplary IFN-L polypeptide selective binding agent of the present invention is capable of binding a certain portion of the IFN-L polypeptide thereby inhibiting the binding of the polypeptide to an IFN-L polypeptide receptor.

Selective binding agents such as antibodies and antibody fragments that bind IFN-L polypeptides are within the scope of the present invention. The antibodies may be polyclonal including monospecific polyclonal; monoclonal (MAbs); recombinant; chimeric; humanized, such as CDR-grafted; human; single chain; and/or bispecific; as well as fragments; variants; or derivatives thereof. Antibody fragments include those portions of the antibody that bind to an epitope on the IFN-L polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an IFN-L polypeptide generally are produced in animals (e.g., rabbits or mice) by means of multiple subcutaneous or intraperitoneal injections of IFN-L polypeptide and an adjuvant. It may be useful to conjugate an IFN-L polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-IFN-L antibody titer.

Monoclonal antibodies directed toward IFN-L polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with IFN-L polypeptides.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al, 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region (CDR) for the corresponding regions of a human antibody.

Also encompassed by the invention are human antibodies that bind IFN-L polypeptides. Using transgenic animals (e.g., mice) that are capable of producing a repertoire of human antibodies in the absence of endogenous immunoglobulin production such antibodies are produced by immunization with an IFN-L polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then crossbred to obtain an animal having all of the desired immune system modifications. When administered an immunogen, these transgenic animals produce antibodies with human (rather than, e.g., murine) amino acid sequences, including variable regions which are immunospecific for these antigens. See PCT App. Nos. PCT/US96/05928 and PCT/US93/06926. Additional methods are described in U.S. Pat. No. 5,545,807, PCT App. Nos. PCT/US91/245 and PCT/GB89/01207, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-IFN-L antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of IFN-L polypeptides. The antibodies will bind IFN-L polypeptides with an affinity that is appropriate for the assay method being employed.

For diagnostic applications, in certain embodiments, anti-IFN-L antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., an IFN-L polypeptide, or an immunologically reactive portion thereof) to compete with the test sample analyte (an IFN-L polypeptide) for binding with a limited amount of anti-IFN-L antibody. The amount of an IFN-L polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-IFN-L antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of an IFN-L polypeptide. In one embodiment, antagonist antibodies of the invention are antibodies or binding fragments thereof which are capable of specifically binding to an IFN-L polypeptide and which are capable of inhibiting or eliminating the functional activity of an IFN-L polypeptide in vivo or in vitro. In preferred embodiments, the selective binding agent, e.g., an antagonist antibody, will inhibit the functional activity of an IFN-L polypeptide by at least about 50%, and preferably by at least about 80%. In another embodiment, the selective binding agent may be an anti-IFN-L polypeptide antibody that is capable of interacting with an IFN-L polypeptide binding partner (a ligand or receptor) thereby inhibiting or eliminating IFN-L polypeptide activity in vitro or in vivo. Selective binding agents, including agonist and antagonist anti-IFN-L polypeptide antibodies, are identified by screening assays that are well known in the art.

The invention also relates to a kit comprising IFN-L selective binding agents (such as antibodies) and other reagents useful for detecting IFN-L polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the IFN-L molecules of the invention, including, but not limited to: the identification and validation of IFN-L disease-related genes as targets for therapeutics; molecular toxicology of related IFN-L molecules and inhibitors thereof; stratification of populations and generation of surrogate markers for clinical trials; and enhancing related IFN-L polypeptide small molecule drug discovery by aiding in the identification of selective compounds in high throughput screens.

Chemical Derivatives

Chemically modified derivatives of IFN-L polypeptides may be prepared by one skilled in the art, given the disclosures described herein. IFN-L polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of either SEQ ID NO: 2 or SEQ ID NO: 5, or other IFN-L polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules which may be used to prepare covalently attached IFN-L polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of either SEQ ID NO: 2 or SEQ ID NO: 5, or other IFN-L polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the IFN-L polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252, 714).

In another embodiment, IFN-L polypeptides may be chemically coupled to biotin. The biotin/IFN-L polypeptide molecules are then allowed to bind to avidin, resulting in tetravalent avidin/biotin/IFN-L polypeptide molecules. IFN-L polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present IFN-L polypeptide derivatives include those described herein for IFN-L polypeptides. However, the IFN-L polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native IFN-L polypeptide have been disrupted (i.e., "knocked out") such that the level of expression of IFN-L polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of an IFN-L gene for that animal or a heterologous IFN-L gene is over-expressed by the animal, thereby creating a "transgenic" animal. Such transgenic animals may be prepared using well known methods such as those described in U.S. Pat. No. 5,489,743 and PCT Pub. No. WO 94/28122.

The present invention further includes non-human animals in which the promoter for one or more of the IFN-L polypeptides of the present invention is either activated or inactivated (e.g., by using homologous recombination methods) to alter the level of expression of one or more of the native IFN-L polypeptides.

These non-human animals may be used for drug candidate screening. In such screening, the impact of a drug candidate on the animal may be measured. For example, drug candidates may decrease or increase the expression of the IFN-L gene. In certain embodiments, the amount of IFN-L polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Other Modulators of IFN-L Polypeptide Activity

In some situations, it may be desirable to identify molecules that are modulators, i.e., agonists or antagonists, of the activity of IFN-L polypeptide. Natural or synthetic molecules that modulate IFN-L polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of an IFN-L polypeptide. Most commonly, a test molecule will interact directly with an IFN-L polypeptide. However, it is also contemplated that a test molecule may also modulate IFN-L polypeptide activity indirectly, such as by affecting IFN-L gene expression, or by binding to an IFN-L polypeptide binding partner (e.g., receptor or ligand). In one embodiment, a test molecule will bind to an IFN-L polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with IFN-L polypeptides are encompassed by the present invention. In certain embodiments, an IFN-L polypeptide is incubated with a test molecule under conditions that permit the interaction of the test molecule with an IFN-L polypeptide, and the extent of the interaction is measured. The test molecule can be screened in a substantially purified form or in a crude mixture.

In certain embodiments, an IFN-L polypeptide agonist or antagonist may be a protein, peptide, carbohydrate, lipid, or small molecular weight molecule that interacts with IFN-L polypeptide to regulate its activity. Molecules which regulate IFN-L polypeptide expression include nucleic acids which are complementary to nucleic acids encoding an IFN-L polypeptide, or are complementary to nucleic acids sequences which direct or control the expression of IFN-L polypeptide, and which act as anti-sense regulators of expression.

Once a test molecule has been identified as interacting with an IFN-L polypeptide, the molecule may be further evaluated for its ability to increase or decrease IFN-L polypeptide activity. The measurement of the interaction of a test molecule with IFN-L polypeptide may be carried out in several formats, including cell-based binding assays, membrane binding assays, solution-phase assays, and immunoassays. In general, a test molecule is incubated with an IFN-L polypeptide for a specified period of time, and IFN-L polypeptide activity is determined by one or more assays for measuring biological activity.

The interaction of test molecules with IFN-L polypeptides may also be assayed directly using polyclonal or monoclonal antibodies in an immunoassay. Alternatively, modified forms of IFN-L polypeptides containing epitope tags as described herein may be used in solution and immunoassays.

In the event that IFN-L polypeptides display biological activity through an interaction with a binding partner (e.g., a receptor or a ligand), a variety of in vitro assays may be used to measure the binding of an IFN-L polypeptide to the corresponding binding partner (such as a selective binding agent, receptor, or ligand). These assays may be used to screen test molecules for their ability to increase or decrease the rate and/or the extent of binding of an IFN-L polypeptide to its binding partner. In one assay, an IFN-L polypeptide is immobilized in the wells of a microtiter plate. Radiolabeled IFN-L polypeptide binding partner (for example, iodinated IFN-L polypeptide binding partner) and a test molecule can then be added either one at a time (in either order) or simultaneously to the wells. After incubation, the wells can be washed and counted for radioactivity, using a scintillation counter, to determine the extent to which the binding partner bound to the IFN-L polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing IFN-L polypeptide binding partner to the microtiter plate wells, incubating with the test molecule and radiolabeled IFN-L polypeptide, and determining the extent of IFN-L polypeptide binding. See, e.g., *Current Protocols in Molecular Biology*, chap. 18 (Ausubel et al., eds., Green Publishers Inc. and Wiley and Sons 1995).

As an alternative to radiolabeling, an IFN-L polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to an IFN-L polypeptide or to an IFN-L polypeptide binding partner, and which is conjugated to biotin, may also be used for purposes of detection following incubation of the complex with enzyme-linked streptavidin linked to AP or HRP.

A IFN-L polypeptide or an IFN-L polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between an IFN-L polypeptide and its binding partner can be assessed using the methods described herein. Alternatively, the substrate-protein complex can be immobilized in a column with the test molecule and complementary protein passing through the column. The formation of a complex between an IFN-L polypeptide and its binding partner can then be assessed using any of the techniques described herein (e.g., radiolabelling or antibody binding).

Another in vitro assay that is useful for identifying a test molecule which increases or decreases the formation of a complex between an IFN-L polypeptide binding protein and an IFN-L polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either IFN-L polypeptide or an IFN-L polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between an IFN-L polypeptide and an IFN-L polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between an IFN-L polypeptide and IFN-L polypeptide binding partner. The assays may be automated to screen compounds generated in phage display, synthetic peptide, and chemical synthesis libraries.

Compounds which increase or decrease the formation of a complex between an IFN-L polypeptide and an IFN-L polypeptide binding partner may also be screened in cell culture using cells and cell lines expressing either IFN-L polypeptide or IFN-L polypeptide binding partner. Cells and cell lines may be obtained from any mammal, but preferably will be from human or other primate, canine, or rodent sources. The binding of an IFN-L polypeptide to cells expressing IFN-L polypeptide binding partner at the surface is evaluated in the presence or absence of test molecules, and the extent of binding may be determined by, for example, flow cytometry using a biotinylated antibody to an IFN-L polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the IFN-L gene. In certain embodiments, the amount of IFN-L polypeptide or an IFN-L polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664-68. For example, an 11 amino acid sequence (Y-G-R-K-K-R-R-Q-R-R-R; SEQ ID NO: 18) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 19), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, an IFN-L antagonist (such as an anti-IFN-L selective binding agent, small molecule, soluble receptor, or antisense oligonucleotide) can be administered intracellularly to inhibit the activity of an IFN-L molecule. As used herein, the term "IFN-L molecule" refers to both IFN-L nucleic acid molecules and IFN-L polypeptides as defined herein. Where desired, the IFN-L protein itself may also be internally administered to a cell using these procedures. See also, Straus, 1999, *Science* 285:1466-67.

Cell Source Identification Using IFN-L Polypeptide

In accordance with certain embodiments of the invention, it may be useful to be able to determine the source of a certain cell type associated with an IFN-L polypeptide. For example, it may be useful to determine the origin of a disease or pathological condition as an aid in selecting an appropriate therapy. In certain embodiments, nucleic acids encoding an IFN-L polypeptide can be used as a probe to identify cells described herein by screening the nucleic acids of the cells with such a probe. In other embodiments, one may use anti-IFN-L polypeptide antibodies to test for the presence of IFN-L polypeptide in cells, and thus, determine if such cells are of the types described herein.

IFN-L Polypeptide Compositions and Administration

Therapeutic compositions are within the scope of the present invention. Such IFN-L polypeptide pharmaceutical compositions may comprise a therapeutically effective amount of an IFN-L polypeptide or an IFN-L nucleic acid molecule in admixture with a pharmaceutically or physiologically acceptable formulation agent selected for suitability with the mode of administration. Pharmaceutical compositions may comprise a therapeutically effective amount of one or more IFN-L polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended route of administration, delivery format, and desired dosage. See, e.g., *Remington's Pharmaceutical Sciences*, supra. Such compositions may influence the physical state, stability, rate of in vivo release, and rate of in vivo clearance of the IFN-L molecule.

The primary vehicle or carrier in a pharmaceutical composition may be either aqueous or non-aqueous m nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, IFN-L polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the IFN-L polypeptide product may be formulated as a lyophilizate using appropriate excipients such as sucrose.

The IFN-L polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired IFN-L molecule in a pharmaceutically acceptable vehicle. A particularly suitable vehicle for parenteral injection is sterile distilled water in which an IFN-L molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, IFN-L polypeptide may be formulated as a dry powder for inhalation. IFN-L polypeptide or nucleic acid molecule inhalation solutions may also be formulated with a propellant for aerosol delivery. In yet another embodiment, solutions may be nebulized. Pulmonary administration is further described in PCT Pub. No. WO 94/20069, which describes the pulmonary delivery of chemically modified proteins.

It is also contemplated that certain formulations may be administered orally. In one embodiment of the present invention, IFN-L polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the IFN-L polypeptide. Diluents, flavorings, low melting point waxes, vegetable oils, lubricants, suspending agents, tablet disintegrating agents, and binders may also be employed.

Another pharmaceutical composition may involve an effective quantity of IFN-L polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional IFN-L polypeptide pharmaceutical compositions will be evident to those skilled in the art, including formulations involving IFN-L polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(−)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The IFN-L pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of an IFN-L pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the IFN-L molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the IFN-L molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use IFN-L polypeptide pharmaceutical compositions in an ex vivo manner. In such instances, cells, tissues, or organs that have been removed from the patient are exposed to IFN-L polypeptide pharmaceutical compositions after which the cells, tissues, or organs are subsequently implanted back into the patient.

In other cases, an IFN-L polypeptide can be delivered by implanting certain cells that have been genetically engineered, using methods such as those described herein, to express and secrete the IFN-L polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more IFN-L polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent IFN-L gene, or an under-expressed gene, and thereby produce a cell which expresses therapeutically efficacious amounts of IFN-L polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. U.S.A.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; PCT/US90/07642, and PCT Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of an IFN-L polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired IFN-L polypeptide. The control element controls a portion of the DNA present in the host cell genome. Thus, the expression of the desired IFN-L polypeptide may be achieved not by transfection of DNA that encodes the IFN-L gene itself, but rather by the use of targeting DNA (containing regions of homology with the endogenous gene of interest) coupled with DNA regulatory segments that provide the endogenous gene sequence with recognizable signals for transcription of an IFN-L gene.

In an exemplary method, the expression of a desired targeted gene in a cell (i.e., a desired endogenous cellular gene) is altered via homologous recombination into the cellular genome at a preselected site, by the introduction of DNA which includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, IFN-L polypeptide production from a cell's endogenous IFN-L gene involves first using homologous recombination to place a recombination sequence from a site-specific recombination system (e.g., Cre/loxP, FLP/FRT) (Sauer, 1994, *Curr. Opin. Biotechnol.*, 5:521-27; Sauer, 1993, *Methods Enzymol.*, 225:890-900) upstream of (i.e., 5' to) the cell's endogenous genomic IFN-L polypeptide coding region. A plasmid containing a recombination site homologous to the site that was placed just upstream of the genomic IFN-L polypeptide coding region is introduced into the modified cell line along with the appropriate recombinase enzyme. This recombinase causes the plasmid to integrate, via the plasmid's recombination site, into the recombination site located just upstream of the genomic IFN-L polypeptide coding region in the cell line (Baubonis and Sauer, 1993, *Nucleic Acids Res.* 21:2025-29; O'Gorman et al., 1991, *Science* 251:1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased IFN-L polypeptide production from the cell's endogenous IFN-L gene.

A further method to use the cell line in which the site specific recombination sequence had been placed just upstream of the cell's endogenous genomic IFN-L polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.*, 5:521-27; Sauer, 1993, *Methods Enzymol.*, 225:890-900) that would create a new or modified transcriptional unit resulting in de novo or increased IFN-L polypeptide production from the cell's endogenous IFN-L gene.

An additional approach for increasing, or causing, the expression of IFN-L polypeptide from a cell's endogenous IFN-L gene involves increasing, or causing, the expression of a gene or genes (e.g., transcription factors) and/or decreasing the expression of a gene or genes (e.g., transcriptional repressors) in a manner which results in de novo or increased IFN-L polypeptide production from the cell's endogenous IFN-L gene. This method includes the introduction of a non-naturally occurring polypeptide (e.g., a polypeptide comprising a site specific DNA binding domain fused to a transcriptional factor domain) into the cell such that de novo or increased IFN-L polypeptide production from the cell's endogenous IFN-L gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of IFN-L polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding an IFN-L polypeptide, which nucleotides may be used as targeting sequences.

IFN-L polypeptide cell therapy, e.g., the implantation of cells producing IFN-L polypeptides, is also contemplated. This embodiment involves implanting cells capable of synthesizing and secreting a biologically active form of IFN-L polypeptide. Such IFN-L polypeptide-producing cells can be cells that are natural producers of IFN-L polypeptides or may be recombinant cells whose ability to produce IFN-L polypeptides has been augmented by transformation with a gene encoding the desired IFN-L polypeptide or with a gene augmenting the expression of IFN-L polypeptide. Such a modification may be accomplished by means of a vector suitable for delivering the gene as well as promoting its expression and secretion. In order to minimize a potential immunological reaction in patients being administered an IFN-L polypeptide, as may occur with the administration of a polypeptide of a foreign species, it is preferred that the natural cells producing IFN-L polypeptide be of human origin and produce human IFN-L polypeptide. Likewise, it is preferred that the recombinant cells producing IFN-L polypeptide be transformed with an expression vector containing a gene encoding a human IFN-L polypeptide.

Implanted cells may be encapsulated to avoid the infiltration of surrounding tissue. Human or non-human animal cells may be implanted in patients in biocompatible, semipermeable polymeric enclosures or membranes that allow the release of IFN-L polypeptide, but that prevent the destruction of the cells by the patient's immune system or by other detrimental factors from the surrounding tissue. Alternatively, the patient's own cells, transformed to produce IFN-L polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (PCT Pub. No. WO 95/05452 and PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of IFN-L polypeptides is also envisioned. One example of a gene therapy technique is to use the IFN-L gene (either genomic DNA, cDNA, and/or synthetic DNA) encoding an IFN-L polypeptide which may be operably linked to a constitutive or inducible promoter to form a "gene therapy DNA construct." The promoter may be homologous or heterologous to the endogenous IFN-L gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the IFN-L gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and PCT Pub. Nos. WO 96/40911 and WO 97/10337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and PCT Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding IFN-L polypeptide into cells via local injection of an IFN-L nucleic acid molecule or by other appropriate viral or non-viral delivery vectors. Hefti, 1994, *Neurobiology* 25:1418-35. For example, a nucleic acid molecule encoding an IFN-L polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome typically contains AAV inverted terminal repeats flanking a DNA sequence encoding an IFN-L polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. Nos. 5,631,236 (involving adenoviral vectors), 5,672,510 (involving retroviral vectors), 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that IFN-L gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous IFN-L polypeptide expression in a cell via gene therapy is to insert one or more enhancer elements into the IFN-L polypeptide promoter, where the enhancer elements can serve to increase transcriptional activity of the IFN-L gene. The enhancer elements used will be selected based on the tissue in which one desires to activate the gene—enhancer elements known to confer promoter activation in that tissue will be selected. For example, if a gene encoding an IFN-L polypeptide is to be "turned on" in T-cells, the lck promoter enhancer element may be used. Here, the functional portion of the transcriptional element to be added may be inserted into a fragment of DNA containing the IFN-L polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease IFN-L polypeptide expression by modifying the nucleotide sequence of the endogenous promoter. Such modification is typically accomplished via homologous recombination methods. For example, a DNA molecule containing all or a portion of the promoter of the IFN-L gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding IFN-L gene. The deletion of the TATA box or the transcription activator binding site in the promoter may be accomplished by generating a DNA construct comprising all or the relevant portion of the IFN-L polypeptide promoter (from the same or a related species as the IFN-L gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

IFN-L nucleic acid molecules, polypeptides, and agonists and antagonists thereof can be used to treat, diagnose, ameliorate, or prevent a number of diseases, disorders, or conditions, including those recited herein.

IFN-L polypeptide agonists and antagonists include those molecules which regulate IFN-L polypeptide activity and either increase or decrease at least one activity of the mature form of the IFN-L polypeptide. Agonists or antagonists may be co-factors, such as a protein, peptide, carbohydrate, lipid, or small molecular weight molecule, which interact with IFN-L polypeptide and thereby regulate its activity. Potential polypeptide agonists or antagonists include antibodies that react with either soluble or membrane-bound forms of IFN-L polypeptides that comprise part or all of the extracellular domains of the said proteins. Molecules that regulate IFN-L polypeptide expression typically include nucleic acids encoding IFN-L polypeptide that can act as anti-sense regulators of expression.

IFN-L polypeptides may play a role in contolling the growth and maintenance of cancer cells based on the homology of IFN-L polypeptides to known interferons. Accordingly, IFN-L nucleic acid molecules, polypeptides, and agonists and antagonists thereof may be useful for the diagnosis and/or treatment of cancer. Examples of such cancers include, but are not limited to, chronic myelogenous leukemia, hairy cell leukemia, Kaposi's sarcoma, melanomas, lung cancer, brain cancer, breast cancer, cancers of the hematopoetic system, prostate cancer, ovarian cancer, and testicular cancer. Other cancers are encompassed within the scope of the invention.

IFN-L polypeptides may play a role in the modulation of the immune system based on the homology of IFN-polypeptides to known interferons. Accordingly, IFN-L nucleic acid molecules, polypeptides, and agonists and antagonists thereof may be useful for the diagnosis and/or treatment of dysfunction of the immune system. Examples of such diseases include, but are not limited to, multiple sclerosis, rheumatoid arthritis, psioriatic arthritis, inflammatory arthritis, osteoarthritis, inflammatory joint disease, autoimmune disease, lupus, diabetes, inflammatory bowel disease, transplant rejection, and graft vs. host disease. Other diseases influenced by the dysfunction of the immune system are encompassed within the scope of the invention.

IFN-L polypeptides may play a role in the control of viral and microbial infections based on the homology of IFN-polypeptides to known interferons. Accordingly, IFN-L nucleic acid molecules, polypeptides, and agonists and antagonists thereof may be useful for the diagnosis and/or treatment of infections. Examples of such diseases include, but are not limited to, hepatitis, human immunodeficiency virus, human papilloma virus, and chronic granulamatous. Other diseases caused by infections are encompassed within the scope of the invention.

IFN-L polypeptides may play a role in the control of bone formation and maintenance based on the homology of IFN-polypeptides to known interferons. Accordingly, IFN-L nucleic acid molecules, polypeptides, and agonists and antagonists may be useful for the diagnosis and/or treatment of bone disorders. Examples of such diseases include, but are not limited to, osteoporosis, osteopetrosis, osteogenesis imperfecta, Paget's disease, periodontal disease, and hypercalcemia. Other bone disorders are encompassed within the scope of the invention.

IFN-L polypeptides may play a role in the inappropriate proliferation of cells based on the homology of IFN-polypeptides to known interferons. Accordingly, IFN-L nucleic acid molecules, polypeptides, and agonists and antagonists may be useful for the diagnosis and/or treatment of diseases where there is abnormal cell proliferation. Examples of such diseases include, but are not limited to, arteriosclerosis and vascular restenosis. Other diseases influenced by the inappropriate proliferation of cells are encompassed within the scope of the invention.

In a specific embodiment, the present invention is directed to the use of an IFN-L polypeptide in combination (pretreatment, post-treatment, or concurrent treatment) with secreted or soluble human fas antigen or recombinant versions thereof (PCT Pub. No. WO 96/20206; Mountz et al., 1995, *J. Immunol.*, 155:4829-37; and European Patent No. 510691). PCT Pub. No. WO 96/20206 discloses secreted human fas antigen (native and recombinant, including an Ig fusion protein), methods for isolating the genes responsible for coding the soluble recombinant human fas antigen, methods for cloning the gene in suitable vectors and cell types, and methods for expressing the gene to produce the inhibitors. European Patent No. 510691 teaches nucleic acids coding for human fas antigen, including soluble fas antigen, vectors expressing for said nucleic acids, and transformants transfected with the vector. When administered parenterally, doses of a secreted or soluble fas antigen fusion protein each are generally from about 1 µg/kg to about 100 µg/kg.

Treatment of the diseases and disorders recited herein can include the use of first line drugs for control of pain and inflammation; these drugs are classified as non-steroidal, anti-inflammatory drugs (NSAIDs). Secondary treatments include corticosteroids, slow acting antirheumatic drugs (SAARDs), or disease modifying (DM) drugs. Information regarding the following compounds can be found in *The Merck Manual of Diagnosis and Therapy* (16th ed. 1992) and in *Pharmaprojects* (PJB Publications Ltd).

In a specific embodiment, the present invention is directed to the use of an IFN-L polypeptide and any of one or more NSAIDs for the treatment of the diseases and disorders recited herein, including acute and chronic inflammation such as rheumatic diseases, and graft versus host disease. NSAIDs owe their anti-inflammatory action, at least in part, to the inhibition of prostaglandin synthesis (Goodman and Gilman, *The Pharmacological Basis of Therapeutics* (7th ed. 1985)). NSAIDs can be characterized into at least nine groups: (1) salicylic acid derivatives, (2) propionic acid derivatives, (3) acetic acid derivatives, (4) fenamic acid derivatives, (5) carboxylic acid derivatives, (6) butyric acid derivatives, (7) oxicams, (8) pyrazoles, and (9) pyrazolones.

In another specific embodiment, the present invention is directed to the use of an IFN-L polypeptide in combination (pretreatment, post-treatment, or concurrent treatment) with any of one or more salicylic acid derivatives, prodrug esters, or pharmaceutically acceptable salts thereof. Such salicylic acid derivatives, prodrug esters, and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate, sodium salicylate and sulfasalazine. Structurally related salicylic acid derivatives having similar analgesic and anti-inflammatory properties are also intended to be encompassed by this group.

In an additional specific embodiment, the present invention is directed to the use of an IFN-L polypeptide in combination (pretreatment, post-treatment, or concurrent treatment) with any of one or more propionic acid derivatives; prodrug esters, or pharmaceutically acceptable salts thereof. The propionic acid derivatives, prodrug esters, and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In yet another specific embodiment, the present invention is directed to the use of an IFN-L polypeptide in combination (pretreatment, post-treatment, or concurrent treatment) with any of one or more acetic acid derivatives, prodrug esters, or pharmaceutically acceptable salts thereof. The acetic acid derivatives, prodrug esters, and pharmaceutically acceptable salts thereof comprise: acemetacin, alclofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In another specific embodiment, the present invention is directed to the use of an IFN-L polypeptide in combination (pretreatment, post-treatment, or concurrent treatment) with any of one or more fenamic acid derivatives, prodrug esters, or pharmaceutically acceptable salts thereof. The fenamic acid derivatives, prodrug esters, and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In an additional specific embodiment, the present invention is directed to the use of an IFN-L polypeptide in combination (pretreatment, post-treatment, or concurrent treatment) with any of one or more carboxylic acid derivatives, prodrug esters, or pharmaceutically acceptable salts thereof. The carboxylic acid derivatives, prodrug esters, and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In yet another specific embodiment, the present invention is directed to the use of an IFN-L polypeptide in combination (pretreatment, post-treatment, or concurrent treatment) with any of one or more butyric acid derivatives, prodrug esters, or pharmaceutically acceptable salts thereof. The butyric acid derivatives, prodrug esters, and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In another specific embodiment, the present invention is directed to the use of an IFN-L polypeptide in combination (pretreatment, post-treatment, or concurrent treatment) with any of one or more oxicams, prodrug esters, or pharmaceutically acceptable salts thereof. The oxicams, prodrug esters, and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In still another specific embodiment, the present invention is directed to the use of an IFN-L polypeptide in combination (pretreatment, post-treatment, or concurrent treatment) with any of one or more pyrazoles, prodrug esters, or pharmaceutically acceptable salts thereof. The pyrazoles, prodrug esters, and pharmaceutically acceptable salts thereof which may be used comprise: difenamizole and epirizole. Structurally related pyrazoles having similar analgesic and anti-inflammatory properties are also intended to be encompassed by this group.

In an additional specific embodiment, the present invention is directed to the use of an IFN-L polypeptide in combination (pretreatment, post-treatment or, concurrent treatment) with any of one or more pyrazolones, prodrug esters, or pharmaceutically acceptable salts thereof. The pyrazolones, prodrug esters, and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In another specific embodiment, the present invention is directed to the use of an IFN-L polypeptide in combination (pretreatment, post-treatment, or concurrent treatment) with any of one or more of the following: NSAIDs: ε-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In still another specific embodiment, the present invention is directed to the use of an IFN-L polypeptide in combination (pretreatment, post-treatment or concurrent treatment) with any of one or more corticosteroids, prodrug esters, or pharmaceutically acceptable salts thereof for the treatment of the diseases and disorders recited herein, including acute and chronic inflammation such as rheumatic diseases, graft versus host disease, and multiple sclerosis. Corticosteroids, prodrug esters, and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluorocinolone acetonide, fluocortin butyl, fluocortolone, fluocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In another specific embodiment, the present invention is directed to the use of an IFN-L polypeptide in combination (pretreatment, post-treatment, or concurrent treatment) with any of one or more slow-acting antirheumatic drugs (SAARDs) or disease modifying antirheumatic drugs (DMARDS), prodrug esters, or pharmaceutically acceptable salts thereof for the treatment of the diseases and disorders recited herein, including acute and chronic inflammation such as rheumatic diseases, graft versus host disease, and multiple sclerosis. SAARDs or DMARDS, prodrug esters, and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxychloroquine sulfate, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In another specific embodiment, the present invention is directed to the use of an IFN-L polypeptide in combination (pretreatment, post-treatment, or concurrent treatment) with any of one or more COX2 inhibitors, prodrug esters, or pharmaceutically acceptable salts thereof for the treatment of the diseases and disorders recited herein, including acute and chronic inflammation. Examples of COX2 inhibitors, prodrug esters, or pharmaceutically acceptable salts thereof include, for example, celecoxib. Structurally related COX2 inhibitors having similar analgesic and anti-inflammatory properties are also intended to be encompassed by this group.

In still another specific embodiment, the present invention is directed to the use of an IFN-L polypeptide in combination (pretreatment, post-treatment, or concurrent treatment) with any of one or more antimicrobials, prodrug esters, or pharmaceutically acceptable salts thereof for the treatment of the diseases and disorders recited herein, including acute and chronic inflammation. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to, penicillin G, penicillin V, methicillin; nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to, cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxone, cephoperazone, ceftazidime, imipenem and aztreonam. The aminoglycosides include, but are not limited to, streptomycin, gentamicin, tobramycin, amikacin, netilmicin, kanamycin and neomycin. The azoles include, but are not limited to, fluconazole. The quinolones include, but are not limited to, nalidixic acid, norfloxacin, enoxacin, ciprofloxacin, ofloxacin, sparfloxacin and temafloxacin. The macrolides include, but are not limited to, erythomycin, spiramycin and azithromycin. The rifamycins include, but are not limited to, rifampin. The tetracyclines include, but are not limited to, spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to, sulfanilamide, sulfamethoxazole, sulfacetamide, sulfadiazine, sulfisoxazole and co-trimoxazole (trimethoprim/sulfamethoxazole). The lincosamides include, but are not limited to, clindamycin and lincomycin. The polymyxins (polypeptides) include, but are not limited to, polymyxin B and colistin.

Agonists or antagonists of IFN-L polypeptide function may be used (simultaneously or sequentially) in combination with one or more cytokines, growth factors, antibiotics, anti-inflammatories, and/or chemotherapeutic agents as is appropriate for the condition being treated.

Other diseases caused by or mediated by undesirable levels of IFN-L polypeptides are encompassed within the scope of the invention. Undesirable levels include excessive levels of IFN-L polypeptides and sub-normal levels of IFN-L polypeptides.

Uses of IFN-L Nucleic Acids and Polypeptides

Nucleic acid molecules of the invention (including those that do not themselves encode biologically active polypeptides) may be used to map the locations of the IFN-L gene and related genes on chromosomes. Mapping may be done by techniques known in the art, such as PCR amplification and in situ hybridization.

IFN-L nucleic acid molecules (including those that do not themselves encode biologically active polypeptides), may be useful as hybridization probes in diagnostic assays to test, either qualitatively or quantitatively, for the presence of an IFN-L nucleic acid molecule in mammalian tissue or bodily fluid samples.

Other methods may also be employed where it is desirable to inhibit the activity of one or more IFN-L polypeptides. Such inhibition may be effected by nucleic acid molecules that are complementary to and hybridize to expression control sequences (triple helix formation) or to IFN-L mRNA. For example, antisense DNA or RNA molecules, which have a sequence that is complementary to at least a portion of an IFN-L gene can be introduced into the cell. Anti-sense probes may be designed by available techniques using the sequence of the IFN-L gene disclosed herein. Typically, each such antisense molecule will be complementary to the start site (5' end) of each selected IFN-L gene. When the antisense molecule then hybridizes to the corresponding IFN-L mRNA, translation of this mRNA is prevented or reduced. Anti-sense inhibitors provide information relating to the decrease or absence of an IFN-L polypeptide in a cell or organism.

Alternatively, gene therapy may be employed to create a dominant-negative inhibitor of one or more IFN-L polypeptides. In this situation, the DNA encoding a mutant polypeptide of each selected IFN-L polypeptide can be prepared and introduced into the cells of a patient using either viral or non-viral methods as described herein. Each such mutant is typically designed to compete with endogenous polypeptide in its biological role.

In addition, an IFN-L polypeptide, whether biologically active or not, may be used as an immunogen, that is, the polypeptide contains at least one epitope to which antibodies may be raised. Selective binding agents that bind to an IFN-L polypeptide (as described herein) may be used for in vivo and in vitro diagnostic purposes, including, but not limited to, use in labeled form to detect the presence of IFN-L polypeptide in a body fluid or cell sample. The antibodies may also be used to prevent, treat, or diagnose a number of diseases and disorders, including those recited herein. The antibodies may bind to an IFN-L polypeptide so as to diminish or block at least one activity characteristic of an IFN-L polypeptide, or may bind to a polypeptide to increase at least one activity characteristic of an IFN-L polypeptide (including by increasing the pharmacokinetics of the IFN-L polypeptide).

The IFN-L polypeptides of the present invention can be used to clone IFN-L polypeptide receptors, using an expression cloning strategy. Radiolabeled ($^{125}$Iodine) IFN-L polypeptide or affinity/activity-tagged IFN-L polypeptide (such as an Fc fusion or an alkaline phosphatase fusion) can be used in binding assays to identify a cell type or cell line or tissue that expresses IFN-L polypeptide receptors. RNA isolated from such cells or tissues can be converted to cDNA, cloned into a mammalian expression vector, and transfected into mammalian cells (such as COS or 293 cells) to create an expression library. A radiolabeled or tagged IFN-L polypeptide can then be used as an affinity ligand to identify and isolate from this library the subset of cells that express the IFN-L polypeptide receptors on their surface. DNA can then be isolated from these cells and transfected into mammalian cells to create a secondary expression library in which the fraction of cells expressing IFN-L polypeptide receptors is many-fold higher than in the original library. This enrichment process can be repeated iteratively until a single recombinant clone containing an IFN-L polypeptide receptor is isolated. Isolation of the IFN-L polypeptide receptors is useful for identifying or developing novel agonists and antagonists of the IFN-L polypeptide signaling pathway. Such agonists and antagonists include soluble IFN-L polypeptide receptors, anti-IFN-L polypeptide receptor antibodies, small molecules, or antisense oligonucleotides, and they may be used for treating, preventing, or diagnosing one or more of the diseases or disorders described herein.

A deposit of cDNA encoding human IFN-L polypeptide, subcloned into pSPORT1 (Gibco BRL) and transfected into E. coli strain DH10B, having Accession No. PTA-976, were made with the American Type Culture Collection, 10801 University Boulevard, Manassas, Va. 20110-2209 on Nov. 23, 1999.

The following examples are intended for illustration purposes only, and should not be construed as limiting the scope of the invention in any way.

Example 1

Cloning of the Rat IFN-L Polypeptide Gene

Generally, materials and methods as described in Sambrook et al. supra were used to clone and analyze the gene encoding rat IFN-L polypeptide.

Sequences encoding the rat IFN-L polypeptide were isolated from a rat placenta cDNA library by large scale random cDNA sequencing in combination with computer-assisted analysis. To construct the rat placenta cDNA library, rat embryo day 17 [E17] placenta mRNA was prepared by standard methods (Chomczynski and Sacchi, 1987, *Anal. Biochem.* 162:156). Following synthesis using the Superscript Plasmid cDNA kit (Gibco BRL), rat cDNA was subcloned into the Sal I and Not I sites of the pSPORT1 vector (Gibco BRL).

Sequence analysis of the full-length cDNA for rat IFN-L polypeptide indicated that the gene comprises a 573 bp open reading frame encoding a protein of 191 amino acids (FIGS. 1A-1B). The rat IFN-L polypeptide sequence is predicted to contain a signal peptide (FIG. 1A, predicted signal peptide indicated by underline). The rat IFN-L polypeptide sequence was identified as being a novel member of the interferon family of proteins following comparisons of the rat IFN-L polypeptide sequence with protein sequences in the GenBank database.

Example 2

Cloning of the Human IFN-L Polypeptide Gene

Generally, materials and methods as described in Sambrook et al. supra were used to clone and analyze the gene encoding human IFN-L polypeptide.

An examination of the genomic structure of known members of the Interferon gene family revealed that members of this family share a unique intronless structure. Sequences encoding the human IFN-L polypeptide were, therefore, isolated by screening a human genomic DNA library with a probe derived from the rat IFN-L polypeptide gene.

A radioactive rat IFN-L probe was generated by polymerase chain reaction (PCR) amplification of rat IFN-L polypeptide cDNA. Polymerase chain reactions (PCR) were performed using a Perkin-Elmer 9600 thermocycler (PE Biosystems, Foster City, Calif.) and the following reaction conditions: 20 ng of rat IFN-L polypeptide cDNA, 20 pmol each of primers 1795-01 (5'-A-T-G-A-C-A-C-T-G-A-A-G-T-A-T-

T-T-A-T-G-G-3'; SEQ ID NO: 20) and 1795-02 (5'-A-T-T-C-A-T-G-T-T-G-A-G-T-A-G-T-T-T-G-T-A-3'; SEQ ID NO: 21), 1 mmol each of dATP, dTTP, dGTP, 0.01 mmol dCTP, 100 µCi $^{32}$P-dCTP, 4 mM MgCl$_2$, 1×PCR buffer, and 5U Taq polymerase (PE Biosystems). A "cold" PCR reaction (i.e., one not performed in the presence of radioactively labeled dCTP, and utilizing a balanced dNTP mix) was prepared simultaneously with the labeled reaction. Amplification reactions were carried out at 94° C. for 30 seconds, 60° C. for 30 seconds, and 72° C. for 1 minute for 45 cycles. Pooled labeled and unlabeled probe was purified using a Quick Spin G-50 column (Qiagen), boiled at 100° C. for 10 minutes, and chilled on ice for 20 minutes prior to addition to the hybridization solution. Probes with a specific activity of at least 5×10$^5$ cpm/µL were generated using this method.

Sequences encoding the human IFN-L polypeptide were isolated by screening a human lambda genomic DNA library (Stratagene, Cat. No. 946206). For the primary screen, 1×10$^6$ clones were plated at a density of 50,000 colonies/plate and transferred to nitrocellulose filters using standard techniques. Positive clones were re-screened prior to analysis.

The rat IFN-L probe was hybridized to the filters overnight at 42° C. in 30% formamide, 5×SSC, 2×Denhart's, 10 µg/mL salmon sperm DNA, 0.2% SDS, 2 mM EDTA, and 0.1% pyrophosphate. Following hybridization, filters were washed for 30-60 minutes at room temperature in 1×SSC and 0.1% SDS and then for 15 minutes at 55° C. in 0.2×SSC and 0.1% SDS.

Three positive clones were recovered following primary and secondary screening, and lambda phage DNA was prepared by a solid plate culture method. The Not I insert was excised from the clones and ligated into pSPORT1 (Gibco BRL), and these ligations were subsequently used to transform E. coli strain DH 10. Following transformation, plasmids were recovered using a Spin Column plasmid prep kit (Qiagen).

Plasmids derived from the three positive genomic DNA clones were analyzed by Southern blot analysis using the rat IFN-L probe utilized in the genomic DNA library screening. After digesting the recovered plasmid DNA with Hind III, the digested fragments were resolved on an agarose gel, and then transferred to a nylon membrane. Hybridization conditions were identical to those utilized in the genomic DNA library screen. Southern blot analysis indicated that the three positive genomic clones were likely to contain identical genomic inserts. The fragments hybridizing with the rat IFN-L probe were subsequently subcloned into pSPORT1 for sequencing analysis. This analysis confirmed that the three positive genomic DNA clones contained identical genomic inserts.

Sequence analysis of the three genomic clones containing sequences encoding human IFN-L polypeptide indicated that the gene comprises a 621 bp open reading frame encoding a protein of 207 amino acids (FIGS. 2A-2B). The human IFN-L polypeptide sequence is predicted to contain a signal peptide (FIG. 2A, predicted signal peptide indicated by underline). Sequence analysis of IFN-L polypeptide strongly suggests that the protein is a secreted cytokine molecule.

A similarity of 64% was observed between the open reading frame of the human IFN-L gene and that of the rat IFN-L cDNA. FIG. 3 illustrates the amino acid sequence alignment of human IFN-L polypeptide (SEQ ID NO: 2), human IFN-β (SEQ ID NO: 7), and rat IFN-L polypeptide (SEQ ID NO: 4). Human IFN-L polypeptide is 30% identical to human IFN-β. Human IFN-L polypeptide is 40.5% identical to and 50% similar to rat IFN-L polypeptide. All five predicted cysteine residues in human IFN-L polypeptide are perfectly aligned with those in rat 1N-L polypeptide.

Example 3

IFN-L mRNA Expression

Developmental expression patterns of IFN-L mRNA were determined by Northern blot analysis using a $^{32}$P-labeled full-length rat cDNA probe to detect the presence of the IFN-L polypeptide transcript in several different stages of mouse and rat embryos. RNA was isolated from the rat and mouse embryos using the same techniques employed for the construction of the rat placenta cDNA library. Northern blots were prehybridized in 40% formamide, 5×SSC, 1 mM EDTA, and 0.1% for 4 hours at 42° C. The blots were hybridized overnight at 42° C. in the same solution, except for the addition of the rat IFN-L probe. Following hybridization, blots were washed for 30 minutes at 60° C. in 1×SSC and 0.1% SDS.

Expression of IFN-L mRNA was examined in various human tissues by RT-PCR using standard techniques. Human IFN-L mRNA was detected in pancreas, small intestine, prostrate, uterus, thyroid, and placenta.

The expression of IFN-L mRNA is localized by in situ hybridization. A panel of normal embryonic and adult mouse tissues is fixed in 4% paraformaldehyde, embedded in paraffin, and sectioned at 5 µm. Sectioned tissues are permeabilized in 0.2 M HCl, digested with Proteinase K, and acetylated with triethanolamine and acetic anhydride. Sections are prehybridized for 1 hour at 60° C. in hybridization solution (300 mM NaCl, 20 mM Tris-HCl, pH 8.0, 5 mM EDTA, 1×Denhardt's solution, 0.2% SDS, 10 mM DTT, 0.25 mg/ml tRNA, 25 µg/ml polyA, 25 µg/ml polyC and 50% formamide) and then hybridized overnight at 60° C. in the same solution containing 10% dextran and 2×10$^4$ cpm/µl of a $^{33}$P-labeled antisense riboprobe complementary to the human IFN-L gene. The riboprobe is obtained by in vitro transcription of a clone containing human IFN-L cDNA sequences using standard techniques.

Following hybridization, sections are rinsed in hybridization solution, treated with RNaseA to digest unhybridized probe, and then washed in 0.1×SSC at 55° C. for 30 minutes. Sections are then immersed in NTB-2 emulsion (Kodak, Rochester, N.Y.), exposed for 3 weeks at 4° C., developed, and counterstained with hematoxylin and eosin. Tissue morphology and hybridization signal are simultaneously analyzed by darkfield and standard illumination for brain (one sagittal and two coronal sections), gastrointestinal tract (esophagus, stomach, duodenum, jejunum, ileum, proximal colon, and distal colon), pituitary, liver, lung, heart, spleen, thymus, lymph nodes, kidney, adrenal, bladder, pancreas, salivary gland, male and female reproductive organs (ovary, oviduct, and uterus in the female; and testis, epididymus, prostate, seminal vesicle, and vas deferens in the male), BAT and WAT (subcutaneous, peri-renal), bone (femur), skin, breast, and skeletal muscle.

Example 4

Production of IFN-L Polypeptides

A. Expression of IFN-L Polypeptides in Bacteria

PCR was used to amplify template DNA sequences encoding either human or rat IFN-L polypeptide using primers that corresponded to the 5' and 3'ends of the sequence (Table I) and which incorporated restriction enzyme sites to permit insertion of the amplified product into an expression vector. Following amplification, PCR products were gel purified, digested with the appropriate restriction enzymes, and ligated into the expression vector pAMG21 (ATCC No. 98113) using standard recombinant DNA techniques. After the ligation of PCR insert and vector sequences, the ligation reaction mixtures were used to transform an E. coli host strain (e.g., Amgen strain #2596) by electroporation and transformants were selected for kanamycin drug resistance. Plasmid DNA from selected colonies was isolated and subjected to DNA sequencing to confirm the presence of an appropriate insert.

To construct a rat IFN-L polypeptide bacterial expression vector, IFN-L nucleic acid sequences were amplified from a cDNA template using the primers 1825-22 and 1825-21. The PCR product that was obtained following amplification with these primers was inserted into the Nde I and Bam HI sites of pAMG21, and the ligation reaction was then used in bacterial transformation. The resulting bacterial clone was designated Amgen strain #3729. FIG. 4 illustrates the nucleotide sequence of the pAMG21 insert of Amgen strain #3729 and the predicted amino acid sequence encoded by this insert.

A rat IFN-L polypeptide bacterial expression vector, in which the cysteine at position 180 was substituted with a serine residue, was constructed using the primers 1825-22 and 1909-56. The PCR product that was obtained following amplification with these primers was inserted into the Nde I and Bam HI sites of pAMG21, and the ligation reaction was then used in bacterial transformation.

clone was designated Amgen strain #3969. FIG. 7 illustrates the nucleotide sequence of the pAMG21 insert of Amgen strain #3969 and the predicted amino acid sequence encoded by this insert.

A human IFN-L polypeptide bacterial expression vector, expressing an N-terminal variant of human IFN-L polypeptide, was constructed by amplifying plasmid from strain #4047 with the primers 1967-32 and 1967-33 The PCR product that was obtained following amplification with these primers was inserted into the Nde I and Bam HI sites of pAMG21, and the ligation reaction was then used in bacterial transformation. The resulting bacterial clone was designated Amgen strain #4182. FIG. 8 illustrates the nucleotide sequence of the pAMG21 insert of Amgen strain #4182 and the predicted amino acid sequence encoded by this insert.

To generate IFN-L polypeptides, transformed host cells were first incubated in Terrific Broth medium containing 50 µg/mL kanamycin at 30° C. prior to induction of IFN-L polypeptide. Expression of IFN-L polypeptide was induced by the addition of 30 ng/mL N-(3-oxohexanoyl)-dl-homoserine lactone followed by a six hour incubation at either 30° C. or 37° C. Expression of IFN-L polypeptide was evaluated by centrifugation of the culture, resuspension and lysis of the bacterial pellets, and analysis of host cell proteins by SDS-polyacrylamide gel electrophoresis.

TABLE I

| SEQ ID | Oligonucleotide ID | Sequence |
|---|---|---|
| 22 | 1825-22 | 5'-GAATAACATATGTGTGTATATCTCGATCATACTATCTTGGAGAATATG-3' |
| 23 | 1825-21 | 5'-CCGCGGATCCATTAATTCATGTTCAGCAGTTTGTAAAAAATACTGAAACAACGACGAATTTCC-3' |
| 24 | 1909-56 | 5'-CCGCGGATCCATTAATTCATGTTCAGCAGTTTGTAAAAAATACTGAAAGAACGACGAATTTCC-3' |
| 25 | 1967-32 | 5'-TTGATCTAGAAAGGAGGAATAACATATGTGTAACCTGCTGAACGTTCACCTGCGTCGTGTTACCTGG-3' |
| 26 | 1982-14 | 5'-CCGCGGATCCATTATTTACGACGGAACAGAGCGGTAAATTTGTAAAAGTAGTACAGGCAACGACGATTTCC-3' |
| 27 | 1967-33 | 5'-CCGCGGATCCATTATTTACGACGGAACAGAGCGGTAAATTTGTAAAAGTAGTACAGAGAACGACGGATTTCC-3' |
| 28 | 2103-87 | 5'-AAGGAGCATATGCTGGACTGTAACCTGCTGAACGTTCAC-3' |
| 29 | 1200-54 | 5'-GTTATTGCTCAGCGGTGGCA-3' |

The resulting bacterial clone was designated Amgen strain #3858. FIG. 5 illustrates the nucleotide sequence of the pAMG21 insert of Amgen strain #3858 and the predicted amino acid sequence encoded by this insert.

To construct a human IFN-L polypeptide bacterial expression vector, IFN-L nucleic acid sequences were amplified from a cDNA template using the primers 1967-32 and 1982-14. The PCR product that was obtained following amplification with these primers was inserted into the Xba I and Bam HI sites of pAMG21, and the ligation reaction was then used in bacterial transformation. The resulting bacterial clone was designated Amgen strain #4047. FIG. 6 illustrates the nucleotide sequence of the pAMG21 insert of Amgen strain #4047 and the predicted amino acid sequence encoded by this insert.

A human IFN-L polypeptide bacterial expression vector, in which the cysteine at position 193 was substituted with a serine residue, was constructed using the primers 1967-32 and 1967-33. The PCR product that was obtained following amplification with these primers was inserted into the Xba I and Bam HI sites of pAMG21, and the ligation reaction was then used in bacterial transformation. The resulting bacterial A single band on an SDS polyacrylamide gel corresponding to E. coli produced IFN-L polypeptide was excised from the gel and N-terminal amino acid sequence was determined essentially as described by Matsudaira et al., 1987, J. Biol. Chem. 262:10-35).

IFN-L polypeptides were purified as follows. Cells were first lysed in water by high pressure homogenization and inclusion bodies were harvested by centrifugation. Solubilized inclusion bodies were then subjected to a variety of refold conditions.

B. Construction of IFN-L Polypeptide Mammalian Expression Vectors

Native protein and native protein-Fc fusion versions of both human and rat IFN-L polypeptides were produced in either a CHO or 293 mammalian expression system. Template DNA sequences encoding IFN-L polypeptide were amplified by PCR using primers corresponding to the 5' and 3'ends (Table II).

To construct IFN-L polypeptide expression vectors, IFN-L nucleic acid sequences were amplified as described below.

Rat IFN-L nucleic acid sequences were obtained using one of three primer pairs (the forward primer 1847-77 and either 1847-88, 1896-56, or 1896-57). A rat IFN-L polypeptide-Fc fusion construct was generated by cloning PCR products prepared with the first set of primers, which incorporated Hind III and Not I cloning sites and no stop codon. Rat IFN-L soluble polypeptides were generated by cloning PCR products prepared with the second set of primers, which incorporated Hind III and Sal I cloning sites and two stop codons, into pDSRα, or the third set of primers, which incorporated Hind III and Not I cloning sites and two stop codons, into pCEP4.

TABLE II

| SEQ ID | Oligonucleotide ID | Sequence |
|---|---|---|
| 30 | 1847-77 | 5'-CCCAAGCTTACCATGACACTGAAGTATTTATG-3' |
| 31 | 1847-78 | 5'-AAGGAAAAAAGCGGCCGCATTCATGTTGAGTAG-3' |
| 32 | 1896-56 | 5'-ACGCGTCGACTCATCAATTCATGTTGAGTAGTTTG-3' |
| 33 | 1896-57 | 5'-AAGGAAAAAAGCGGCCGCTCATCAATTCATGTTGAGTAG-3' |
| 34 | 1954-45 | 5'-ACGCGTCGACTTATTATTTCCTCCTGAATAG-3' |
| 35 | 1954-46 | 5'-AAGGAAAAAAGCGGCCGCTTATTATTTCCTCCTGAATAGAGC-3' |
| 36 | 1955-44 | 5'-CCCAAGCTTACCATGAGCACCAAACCTGATATG-3' |
| 37 | 1954-47 | 5'-CCCAAGCTTACCATGATTCAAAAGTGTTTGTGGC-3' |
| 38 | 1954-48 | 5'-AAGGAAAAAAGCGGCCGCGCGGCCCTCGATTTTCCTCCTGAATAGAGCTGTAA-3' |
| 39 | 1954-49 | 5'-AAGGAAAAAAGCGGCCGCTTTCCTCCTGAATAGAGCTGTAA-3' |

Human IFN-L nucleic acid sequences were obtained using one of three primer pairs (the forward primer 1954-48 and 1954-49 and the forward primer 1955-44 and either 1854-45 or 1854-46). A human IFN-L polypeptide-Fc fusion construct was generated by cloning PCR products prepared with the first set of primers, which incorporated Not I cloning sites, no stop codon, and a Factor Xa cleavage site. Human IFN-L soluble polypeptides were generated by cloning PCR products prepared with the second set of primers, which incorporated Hind III and Sal I cloning sites and two stop codons, into pDSRα, or the third set of primers, which incorporated Hind III and Not I cloning sites and two stop codons, into pCEP4. A second forward primer (1954-47) was also utilized in place of 1955-44 to generate constructs possessing two initiation codons.

PCR amplifications were performed using a Perkin-Elmer 9600 thermocycler and the following reaction conditions: 20 ng of rat or human IFN-L polypeptide cDNA, 20 pmol each of the appropriate primers, 1 mmol of dNTPs, 4 mM $MgCl_2$, 1×PCR buffer, and 5U Taq polymerase (PE Biosystems). Amplification reactions were carried out at 94° C. for 30 seconds, 50° C. for 30 seconds, and 72° C. for 1 minute for 4 cycles followed by 94° C. for 30 seconds, 55° C. for 30 seconds, and 72° C. for 1 minute for 26 cycles.

PCR products were purified using Qiagen PCR purification spin columns and then subjected to digestion with the appropriate restriction endonucleases. Following digestion, fragments were separated on agarose gels, purified using Qiagen gel purification spin columns, and ligated into the appropriate vectors. Ligations were transformed into the *E. coli* strain DH10. Following sequence analysis of selected transformants, large-scale plasmid stocks were prepared for tissue culture transfection.

C. Expression and Purification of IFN-L Polypeptide in Mammalian Cells

IFN-L polypeptide expression constructs were introduced into 293 EBNA or CHO cells using either a lipofection or calcium phosphate protocol.

To conduct functional studies on the IFN-L polypeptides that were produced, large quantities of conditioned media were generated from a pool of hygromycin selected 293 EBNA clones. The cells were cultured in 500 cm Nunc Triple Flasks to 80% confluence before switching to serum free media a week prior to harvesting the media Conditioned media was harvested and frozen at −20° C. until purification.

Conditioned media was purified by affinity chromatography as described below. The media was thawed and then passed through a 0.2 μm filter. A Protein G column was equilibrated with PBS at pH 7.0, and then loaded with the filtered media. The column was washed with PBS until the absorbance at $A_{280}$ reached a baseline. IFN-L polypeptide was eluted from the column with 0.1 M Glycine-HCl at pH 2.7 and immediately neutralized with 1 M Tris-HCl at pH 8.5. Fractions containing IFN-L polypeptide were pooled, dialyzed in PBS, and stored at −70° C.

For Factor Xa cleavage of the human IFN-L polypeptide-Fc fusion polypeptide, affinity chromatography-purified protein was dialyzed in 50 mM Tris-HCl, 100 mM NaCl, 2 mM $CaCl_2$ at pH 8.0. The restriction protease Factor Xa was added to the dialyzed protein at 1/100 (w/w) and the sample digested overnight at room temperature.

Example 5

Biological Activity of IFN-L Polypeptides

The phosphorylation of IFN-L polypeptide was assayed as follows. Cell lines were exposed to 1 μg/mL of the rat IFN-L Fc fusion polypeptide generated in Example 4C or to a control solution at 37° C. for 15 minutes. Following IFN-L polypeptide exposure, the cells were lysed and cellular proteins were recovered and separated by SDS-PAGE. The separated proteins were then analyzed by Western blot using an anti-pTyr antibody. Several cell lines showed an increase in cellular protein phosphorylation following exposure to IFN-L Fc fusion polypeptide.

Example 6

Production of Anti-IFN-L Polypeptide Antibodies

Antibodies to IFN-L polypeptides may be obtained by immunization with purified protein or with IFN-L peptides produced by biological or chemical synthesis. Suitable procedures for generating antibodies include those described in Hudson and Bay, *Practical Immunology* (2nd ed., Blackwell Scientific Publications).

In one procedure for the production of antibodies, animals (typically mice or rabbits) are injected with an IFN-L antigen (such as an IFN-L polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), are first incubated in DMEM with 200 U/mL penicillin, 200 µg/mL streptomycin sulfate, and 4 mM glutamine, and are then incubated in HAT selection medium (hypoxanthine, aminopterin, and thymidine). After selection, the tissue culture supernatants are taken from each fusion well and tested for anti-IFN-L antibody production by ELISA.

Alternative procedures for obtaining anti-IFN-L antibodies may also be employed, such as the immunization of transgenic mice harboring human Ig loci for production of human antibodies, and the screening of synthetic antibody libraries, such as those generated by mutagenesis of an antibody variable domain.

Example 7

Expression of IFN-L Polypeptide in Transgenic Mice

To assess the biological activity of IFN-L polypeptide, a construct encoding an IFN-L polypeptide/Fc fusion protein under the control of a liver specific ApoE promoter is prepared. The delivery of this construct is expected to cause pathological changes that are informative as to the function of IFN-L polypeptide. Similarly, a construct containing the full-length IFN-L polypeptide under the control of the beta actin promoter is prepared. The delivery of this construct is expected to result in ubiquitous expression.

To generate these constructs, PCR is used to amplify template DNA sequences encoding an IFN-L polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified IFN-L polypeptide sequences can be cloned into an expression vector under the control of the human β-actin promoter as described by Graham et al., 1997, *Nature Genetics*, 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The IFN-L polypeptide expression vector is purified through two rounds of CsCl density gradient centrifugation, cleaved with a suitable restriction enzyme, and the linearized fragment containing the IFN-L polypeptide transgene is purified by gel electrophoresis. The purified fragment is resuspended in 5 mM Tris, pH 7.4, and 0.2 mM EDTA at a concentration of 2 mg/mL.

Single-cell embryos from BDF1×BDF1 bred mice are injected as described (PCT Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (Qiagen) and transgene expression determined by RT-PCR. RNA recovered from spleens is converted to cDNA using the SuperScript™ Preamplification System (Gibco-BRL) as follows. A suitable primer, located in the expression vector sequence and 3' to the IFN-L polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each dNTP, 0.1 mM DTT, and 200 U of SuperScript II reverse transcriptase. Following incubation for 50 minutes at 42° C., the reaction is stopped by heating for 15 minutes at 72° C. and digested with 2U of RNase H for 20 minutes at 37° C. Samples are then amplified by PCR using primers specific for IFN-L polypeptide.

Example 8

Biological Activity of IFN-L Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B cell and T cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately 1×10⁶ cells from each tissue are then incubated for 10 minutes with 0.5 μg CD16/32(FcγIII/II) Fc block in a 20 μL volume. Samples are then stained for 30 minutes at 2-8° C. in a 100 μL volume of PBS (lacking Ca⁺ and Mg⁺), 0.1% bovine serum albumin, and 0.01% sodium azide with 0.5 μg antibody of FITC or PE-conjugated monoclonal antibodies against CD90.2 (Thy-1.2), CD45R (B220), CD11b (Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

What is claimed is:

1. An isolated nucleic acid molecule comprising a nucleotide sequence:
   (a) as set forth in SEQ ID NO: 4;
   (b) of the DNA insert in ATCC Deposit No. PTA-976;
   (c) encoding the Interferon-like polypeptide as set forth in SEQ ID NO: 5;
   (d) that hybridizes to the full complement of the nucleotide sequence of any of (a)-(c) at 65° C. in a hybridization buffer comprising 0.015 M NaCl, 0.0015 M sodium citrate, and 0.1% SDS, followed by washing in 6×SSC, 0.1% SDS; or
   (e) fully complementary to the nucleotide sequence of any of (a)-(d).

2. A vector comprising the nucleic acid molecule of claim 1(e).

3. An isolated host cell comprising the vector of claim 2.

4. The host cell of claim 3 that is a eukaryotic cell.

5. The host cell of claim 3 that is a prokaryotic cell.

6. A viral vector comprising a nucleic acid molecule of claim 1.

7. A vector comprising the nucleic acid molecule of any one of claim 1(a)-1(d).

8. An isolated host cell comprising the vector of claim 7.

9. A process of producing a polypeptide comprising culturing the host cell of claim 8 under suitable conditions to express the polypeptide, and optionally isolating the polypeptide from the culture.

10. The process of claim 9, wherein the nucleic acid molecule comprises a heterologous promoter linked to the DNA encoding the Interferon-like polypeptide.

11. The host cell of claim 8 that is a eukaryotic cell.

12. The host cell of claim 8 that is a prokaryotic cell.

* * * * *

SEQUENCE LISTING

<160> NUMBER OF SEQ ID NOS: 39

<210> SEQ ID NO 1
<211> LENGTH: 913
<212> TYPE: DNA
<213> ORGANISM: Rattus norvegicus
<220> FEATURE:
<221> NAME/KEY: CDS
<222> LOCATION: (53)..(625)
<220> FEATURE:
<221> NAME/KEY: sig_peptide
<222> LOCATION: (53)..(115)

<400> SEQUENCE: 1

```
gggtgttgta gatattttc ctttggaaga aatactgagc accaaggctg ag atg aca      58
                                                         Met Thr
                                                          1 ctg aag tat tta tgg ctg gtg gcc ctc gtg gct cta tac att tca ccc     106
Leu Lys Tyr Leu Trp Leu Val Ala Leu Val Ala Leu Tyr Ile Ser Pro
         5                  10                  15 atc cag tct cag aac tgt gtg tat ctg gat cat acc atc ttg gaa aac     154
Ile Gln Ser Gln Asn Cys Val Tyr Leu Asp His Thr Ile Leu Glu Asn
     20                  25                  30 atg aaa ctt ctg agc agc atc agg acc acc ttt ccc tta aga tgt cta     202
Met Lys Leu Leu Ser Ser Ile Arg Thr Thr Phe Pro Leu Arg Cys Leu
 35                  40                  45                  50 aaa gat atc acg gat ttt gag ttt cct caa gag att ctg ctg tac gtc     250
Lys Asp Ile Thr Asp Phe Glu Phe Pro Gln Glu Ile Leu Leu Tyr Val
                 55                  60                  65 cag cat gtg aaa aag gac ata aag gca gtc acc tat cat ata tct tct     298
Gln His Val Lys Lys Asp Ile Lys Ala Val Thr Tyr His Ile Ser Ser
             70                  75                  80 ctg gcg cta att att ttc agt ctt aaa gac tcc atc tcc ctg gcg aca     346
Leu Ala Leu Ile Ile Phe Ser Leu Lys Asp Ser Ile Ser Leu Ala Thr
         85                  90                  95 gag gaa cgc ttg gaa cgt atc aga tcg gga ctt ttc aaa caa gtg cag     394
Glu Glu Arg Leu Glu Arg Ile Arg Ser Gly Leu Phe Lys Gln Val Gln
    100                 105                 110 caa gct cga gag tgc atg gta gac gag gag aac aag aac acg gag gag     442
Gln Ala Arg Glu Cys Met Val Asp Glu Glu Asn Lys Asn Thr Glu Glu
115                 120                 125                 130 gac agt aca tca caa cat cct cac tca gag ggc ttc aag gca gtc tac     490
Asp Ser Thr Ser Gln His Pro His Ser Glu Gly Phe Lys Ala Val Tyr
                 135                 140                 145 ctg gaa ttg aac aag tat ttc ttc aga atc aga aag ttc ctg gta aat     538
Leu Glu Leu Asn Lys Tyr Phe Phe Arg Ile Arg Lys Phe Leu Val Asn
```

```
                    150                 155                 160
aag aaa tac agt ttc tgt gcc tgg aag att gtc gtg gtg gaa ata aga         586
Lys Lys Tyr Ser Phe Cys Ala Trp Lys Ile Val Val Val Glu Ile Arg
            165                 170                 175 aga tgt ttc agt ata ttt tac aaa cta ctc aac atg aat tgagaatcat         635
Arg Cys Phe Ser Ile Phe Tyr Lys Leu Leu Asn Met Asn
        180                 185                 190 ccagcttcaa gcaagaactt agatagaagt tgtgactgct caaatgtccc caagaacgct     695
tgattctaag gctattgcga gtctgctgct acacacttcg gacgcaagac ttttcaaggt     755
cagggttcaa ggtagtacag tcaaaggaag tcttatgtta agcaaaagaa aaatttcagt    815
ggaaaagcta gcagaaatgt caacttgtca aaaaacaac ttatggatta tggcattgac     875
gttactagca aaaaaataa acaaaaaaa aacaaaaa                               913

<210> SEQ ID NO 2
<211> LENGTH: 191
<212> TYPE: PRT
<213> ORGANISM: Rattus norvegicus

<400> SEQUENCE: 2

Met Thr Leu Lys Tyr Leu Trp Leu Val Ala Leu Val Ala Leu Tyr Ile
1               5                   10                  15

Ser Pro Ile Gln Ser Gln Asn Cys Val Tyr Leu Asp His Thr Ile Leu
            20                  25                  30

Glu Asn Met Lys Leu Leu Ser Ser Ile Arg Thr Thr Phe Pro Leu Arg
        35                  40                  45

Cys Leu Lys Asp Ile Thr Asp Phe Glu Phe Pro Gln Glu Ile Leu Leu
    50                  55                  60

Tyr Val Gln His Val Lys Lys Asp Ile Lys Ala Val Thr Tyr His Ile
65                  70                  75                  80

Ser Ser Leu Ala Leu Ile Ile Phe Ser Leu Lys Asp Ser Ile Ser Leu
                85                  90                  95

Ala Thr Glu Glu Arg Leu Glu Arg Ile Arg Ser Gly Leu Phe Lys Gln
            100                 105                 110

Val Gln Gln Ala Arg Glu Cys Met Val Asp Glu Glu Asn Lys Asn Thr
        115                 120                 125

Glu Glu Asp Ser Thr Ser Gln His Pro His Ser Glu Gly Phe Lys Ala
    130                 135                 140

Val Tyr Leu Glu Leu Asn Lys Tyr Phe Arg Ile Arg Lys Phe Leu
145                 150                 155                 160

Val Asn Lys Lys Tyr Ser Phe Cys Ala Trp Lys Ile Val Val Val Glu
                165                 170                 175

Ile Arg Arg Cys Phe Ser Ile Phe Tyr Lys Leu Leu Asn Met Asn
            180                 185                 190

<210> SEQ ID NO 3
<211> LENGTH: 168
<212> TYPE: PRT
<213> ORGANISM: Rattus norvegicus

<400> SEQUENCE: 3

Cys Val Tyr Leu Asp His Thr Ile Leu Glu Asn Met Lys Leu Leu Ser
1               5                   10                  15

Ser Ile Arg Thr Thr Phe Pro Leu Arg Cys Leu Lys Asp Ile Thr Asp
            20                  25                  30

Phe Glu Phe Pro Gln Glu Ile Leu Leu Tyr Val Gln His Val Lys Lys
```

```
                35                  40                  45
Asp Ile Lys Ala Val Thr Tyr His Ile Ser Ser Leu Ala Leu Ile Ile
 50                  55                  60

Phe Ser Leu Lys Asp Ser Ile Ser Leu Ala Thr Glu Glu Arg Leu Glu
 65                  70                  75                  80

Arg Ile Arg Ser Gly Leu Phe Lys Gln Val Gln Gln Ala Arg Glu Cys
                 85                  90                  95

Met Val Asp Glu Glu Asn Lys Asn Thr Glu Glu Asp Ser Thr Ser Gln
            100                 105                 110

His Pro His Ser Glu Gly Phe Lys Ala Val Tyr Leu Glu Leu Asn Lys
        115                 120                 125

Tyr Phe Phe Arg Ile Arg Lys Phe Leu Val Asn Lys Lys Tyr Ser Phe
    130                 135                 140

Cys Ala Trp Lys Ile Val Val Glu Ile Arg Arg Cys Phe Ser Ile
145                 150                 155                 160

Phe Tyr Lys Leu Leu Asn Met Asn
            165

<210> SEQ ID NO 4
<211> LENGTH: 1836
<212> TYPE: DNA
<213> ORGANISM: Homo sapiens
<220> FEATURE:
<221> NAME/KEY: CDS
<222> LOCATION: (575)..(1195)
<220> FEATURE:
<221> NAME/KEY: sig_peptide
<222> LOCATION: (575)..(655)

<400> SEQUENCE: 4
aagcttaatt taacaaaatt ggaaaaacct aaactatact gtgctctggt gacctagcaa      60
tcaaataatc acagtcattt ggtcaatgtc tatgattaac tcaatgagac aggatgtttg     120
gctatagcac caggtacaaa aaatatattt tcatgaagga tcactccctc ttatgtaata    180
gatttgggtg agtgagtgag tgagtgagtg catggactca cagcttttgg ctttctgaaa    240 tacccctgcat cagtcttgtt atgatgattc cttagtgctg ggatggatca tccaggcatt   300
taaggtaaca cgatggtaat tctttgctca tttttcaggg aaaaaaaaaa gttatcactt    360
ccaaagtcgg catagtcacc cgaagtaaaa aaaaaaaaaa aaaaaaaaag cctcagaggc    420
aaaggaaagg ggccgcaacc ttggttaact gtgaaatgac gaatgagaaa actcctcctg    480
ctgaagatat tcaggtatat aaaggcacat gaaggaaaac tcaaacatc attgtcatat     540 acacatcttc tggattttttt agcttgcaaa aaaa atg agc acc aaa cct gat atg    595
                                     Met Ser Thr Lys Pro Asp Met
                                      1               5 att caa aag tgt ttg tgg ctt gag atc ctt atg ggt ata ttc att gct       643
Ile Gln Lys Cys Leu Trp Leu Glu Ile Leu Met Gly Ile Phe Ile Ala
        10                  15                  20 ggc acc cta tcc ctg gac tgt aac tta ctg aac gtt cac ctg aga aga       691
Gly Thr Leu Ser Leu Asp Cys Asn Leu Leu Asn Val His Leu Arg Arg
 25                  30                  35 gtc acc tgg caa aat ctg aga cat ctg agt agt atg agc aat tca ttt       739
Val Thr Trp Gln Asn Leu Arg His Leu Ser Ser Met Ser Asn Ser Phe
 40                  45                  50                  55 cct gta gaa tgt cta cga gaa aac ata gct ttt gag ttg ccc caa gag       787
Pro Val Glu Cys Leu Arg Glu Asn Ile Ala Phe Glu Leu Pro Gln Glu
             60                  65                  70 ttt ctg caa tac acc caa cct atg aag agg gac atc aag aag gcc ttc       835
```

-continued

```
Phe Leu Gln Tyr Thr Gln Pro Met Lys Arg Asp Ile Lys Lys Ala Phe
             75                  80                  85 tat gaa atg tcc cta cag gcc ttc aac atc ttc agc caa cac acc ttc      883
Tyr Glu Met Ser Leu Gln Ala Phe Asn Ile Phe Ser Gln His Thr Phe
         90                  95                 100 aaa tat tgg aaa gag aga cac ctc aaa caa atc caa ata gga ctt gat      931
Lys Tyr Trp Lys Glu Arg His Leu Lys Gln Ile Gln Ile Gly Leu Asp
    105                 110                 115 cag caa gca gag tac ctg aac caa tgc ttg gag gaa gac gag aat gaa      979
Gln Gln Ala Glu Tyr Leu Asn Gln Cys Leu Glu Glu Asp Glu Asn Glu
120                 125                 130                 135 aat gaa gac atg aaa gaa atg aaa gag aat gag atg aaa ccc tca gaa     1027
Asn Glu Asp Met Lys Glu Met Lys Glu Asn Glu Met Lys Pro Ser Glu
                140                 145                 150 gcc agg gtc ccc cag ctg agc agc ctg gaa ctg agg aga tat ttc cac     1075
Ala Arg Val Pro Gln Leu Ser Ser Leu Glu Leu Arg Arg Tyr Phe His
            155                 160                 165 agg ata gac aat ttc ctg aaa gaa aag aaa tac agt gac tgt gcc tgg     1123
Arg Ile Asp Asn Phe Leu Lys Glu Lys Lys Tyr Ser Asp Cys Ala Trp
        170                 175                 180 gag att gtc cga gtg gaa atc aga aga tgt ttg tat tac ttt tac aaa     1171
Glu Ile Val Arg Val Glu Ile Arg Arg Cys Leu Tyr Tyr Phe Tyr Lys
    185                 190                 195 ttt aca gct cta ttc agg agg aaa taaggtatat ttttggaatt aaaattcctt    1225
Phe Thr Ala Leu Phe Arg Arg Lys
200                 205 ttccctccga aatctctttc tccttctcct cctccatctt cttttaagg attgttgtgc    1285 tgtcctgtaa gcctgtcctc agttggactg gtagcctcgg aacatcaggg acactcacct   1345
ctctaaggag aggtaatgcc aaccatcctc agggtgacca agagtctcct tagaaagtct   1405
ttaagacatt tttaaaggaa taagattccc tctccgtctt cttctattct ctcttgctct   1465
tttctgtggc cattttgaaa gagctttgct atatatacca cctgtggact tcaccaagac   1525
aatggctaga ggatagggag cagagaatgt tgcaaaatgg taacatttca atgacttaac   1585
tgttttgctg ccaaggttgc ttatcctatg aaaattcagc acattaaaag agcttataca   1645
tgctccctag agtcaatact cttgcatttt ccccctcctg ctcgggggga aaaggttga    1705 catttctggc ccatttcctt ctcagcttgg tttgtttgaa ttgatgcttg tggaatggta   1765
tttcattact ttaagagtga agatccatag tgaaattgga tggatggttg aattagacga   1825
ccattaagct t                                                        1836

<210> SEQ ID NO 5
<211> LENGTH: 207
<212> TYPE: PRT
<213> ORGANISM: Homo sapiens

<400> SEQUENCE: 5

Met Ser Thr Lys Pro Asp Met Ile Gln Lys Cys Leu Trp Leu Glu Ile
 1               5                  10                  15

Leu Met Gly Ile Phe Ile Ala Gly Thr Leu Ser Leu Asp Cys Asn Leu
             20                  25                  30

Leu Asn Val His Leu Arg Arg Val Thr Trp Gln Asn Leu Arg His Leu
         35                  40                  45

Ser Ser Met Ser Asn Ser Phe Pro Val Glu Cys Leu Arg Glu Asn Ile
    50                  55                  60

Ala Phe Glu Leu Pro Gln Glu Phe Leu Gln Tyr Thr Gln Pro Met Lys
65                  70                  75                  80
```

-continued

Arg Asp Ile Lys Lys Ala Phe Tyr Glu Met Ser Leu Gln Ala Phe Asn
            85                  90                  95

Ile Phe Ser Gln His Thr Phe Lys Tyr Trp Lys Glu Arg His Leu Lys
            100                 105                 110

Gln Ile Gln Ile Gly Leu Asp Gln Gln Ala Glu Tyr Leu Asn Gln Cys
            115                 120                 125

Leu Glu Glu Asp Glu Asn Glu Asn Glu Asp Met Lys Glu Met Lys Glu
        130                 135                 140

Asn Glu Met Lys Pro Ser Glu Ala Arg Val Pro Gln Leu Ser Ser Leu
145                 150                 155                 160

Glu Leu Arg Arg Tyr Phe His Arg Ile Asp Asn Phe Leu Lys Glu Lys
                165                 170                 175

Lys Tyr Ser Asp Cys Ala Trp Glu Ile Val Arg Val Glu Ile Arg Arg
            180                 185                 190

Cys Leu Tyr Tyr Phe Tyr Lys Phe Thr Ala Leu Phe Arg Arg Lys
            195                 200                 205

<210> SEQ ID NO 6
<211> LENGTH: 178
<212> TYPE: PRT
<213> ORGANISM: Homo sapiens

<400> SEQUENCE: 6

Cys Asn Leu Leu Asn Val His Leu Arg Arg Val Thr Trp Gln Asn Leu
1               5                   10                  15

Arg His Leu Ser Ser Met Ser Asn Ser Phe Pro Val Glu Cys Leu Arg
            20                  25                  30

Glu Asn Ile Ala Phe Glu Leu Pro Gln Glu Phe Leu Gln Tyr Thr Gln
            35                  40                  45

Pro Met Lys Arg Asp Ile Lys Lys Ala Phe Tyr Glu Met Ser Leu Gln
        50                  55                  60

Ala Phe Asn Ile Phe Ser Gln His Thr Phe Lys Tyr Trp Lys Glu Arg
65                  70                  75                  80

His Leu Lys Gln Ile Gln Ile Gly Leu Asp Gln Gln Ala Glu Tyr Leu
                85                  90                  95

Asn Gln Cys Leu Glu Glu Asp Glu Asn Glu Asn Glu Asp Met Lys Glu
            100                 105                 110

Met Lys Glu Asn Glu Met Lys Pro Ser Glu Ala Arg Val Pro Gln Leu
        115                 120                 125

Ser Ser Leu Glu Leu Arg Arg Tyr Phe His Arg Ile Asp Asn Phe Leu
    130                 135                 140

Lys Glu Lys Lys Tyr Ser Asp Cys Ala Trp Glu Ile Val Arg Val Glu
145                 150                 155                 160

Ile Arg Arg Cys Leu Tyr Tyr Phe Tyr Lys Phe Thr Ala Leu Phe Arg
                165                 170                 175

Arg Lys

<210> SEQ ID NO 7
<211> LENGTH: 187
<212> TYPE: PRT
<213> ORGANISM: Homo sapiens

<400> SEQUENCE: 7

Met Thr Asn Lys Cys Ile Leu Gln Ile Ala Leu Leu Leu Cys His Ser
1               5                   10                  15

```
Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Lys Leu Thr Gly Tyr Leu Arg Asn
            180                 185

<210> SEQ ID NO 8
<211> LENGTH: 520
<212> TYPE: DNA
<213> ORGANISM: Artificial Sequence
<220> FEATURE:
<223> OTHER INFORMATION: Description of Artificial Sequence: Rat
      IFN-like polypeptide cDNA insert and partial pAMG21 vector
      sequence
<220> FEATURE:
<221> NAME/KEY: CDS
<222> LOCATION: (4)..(510)

<400> SEQUENCE: 8 cat atg tgt gta tat ctc gat cat act atc ttg gag aat atg aaa ctt     48
    Met Cys Val Tyr Leu Asp His Thr Ile Leu Glu Asn Met Lys Leu
    1               5                  10                  15 ctg agc agc atc cgt acc acc ttt cct ctg cgt tgt ctg aaa gat atc     96
Leu Ser Ser Ile Arg Thr Thr Phe Pro Leu Arg Cys Leu Lys Asp Ile
            20                  25                  30 acg gat ttt gag ttt cct caa gag att ctg ctg tac gtc cag cat gtg    144
Thr Asp Phe Glu Phe Pro Gln Glu Ile Leu Leu Tyr Val Gln His Val
        35                  40                  45 aaa aag gac ata aag gca gtc acc tat cat ata tct tct ctg gcg cta    192
Lys Lys Asp Ile Lys Ala Val Thr Tyr His Ile Ser Ser Leu Ala Leu
    50                  55                  60 att att ttc agt ctt aaa gac tcc atc tcc ctg gcg aca gag gaa cgc    240
Ile Ile Phe Ser Leu Lys Asp Ser Ile Ser Leu Ala Thr Glu Glu Arg
65                  70                  75 ttg gaa cgt atc aga tcg gga ctt ttc aaa caa gtg cag caa gct cga    288
Leu Glu Arg Ile Arg Ser Gly Leu Phe Lys Gln Val Gln Gln Ala Arg
80                  85                  90                  95 gag tgc atg gta gac gag gag aac aag aac acg gag gag gac agt aca    336
Glu Cys Met Val Asp Glu Glu Asn Lys Asn Thr Glu Glu Asp Ser Thr
                100                 105                 110 tca caa cat cct cac tca gag ggc ttc aag gca gtc tac ctg gaa ttg    384
Ser Gln His Pro His Ser Glu Gly Phe Lys Ala Val Tyr Leu Glu Leu
            115                 120                 125
```

-continued

```
aac aag tat ttc ttc aga atc aga aag ttc ctg gta aat aag aaa tac      432
Asn Lys Tyr Phe Phe Arg Ile Arg Lys Phe Leu Val Asn Lys Lys Tyr
        130                 135                 140 agt ttc tgt gcc tgg aag att gtc gtg gtg gaa att cgt cgt tgt ttc      480
Ser Phe Cys Ala Trp Lys Ile Val Val Val Glu Ile Arg Arg Cys Phe
145                 150                 155 agt att ttt tac aaa ctg ctg aac atg aat taatggatcc                    520
Ser Ile Phe Tyr Lys Leu Leu Asn Met Asn
160                 165
```

<210> SEQ ID NO 9
<211> LENGTH: 169
<212> TYPE: PRT
<213> ORGANISM: Artificial Sequence
<220> FEATURE:
<223> OTHER INFORMATION: Description of Artificial Sequence: Rat
      IFN-like polypeptide cDNA insert and partial pAMG21 vector
      sequence

<400> SEQUENCE: 9

```
Met Cys Val Tyr Leu Asp His Thr Ile Leu Glu Asn Met Lys Leu Leu
 1               5                  10                  15

Ser Ser Ile Arg Thr Thr Phe Pro Leu Arg Cys Leu Lys Asp Ile Thr
            20                  25                  30

Asp Phe Glu Phe Pro Gln Glu Ile Leu Leu Tyr Val Gln His Val Lys
        35                  40                  45

Lys Asp Ile Lys Ala Val Thr Tyr His Ile Ser Ser Leu Ala Leu Ile
    50                  55                  60

Ile Phe Ser Leu Lys Asp Ser Ile Ser Leu Ala Thr Glu Glu Arg Leu
65                  70                  75                  80

Glu Arg Ile Arg Ser Gly Leu Phe Lys Gln Val Gln Gln Ala Arg Glu
                85                  90                  95

Cys Met Val Asp Glu Glu Asn Lys Asn Thr Glu Glu Asp Ser Thr Ser
            100                 105                 110

Gln His Pro His Ser Glu Gly Phe Lys Ala Val Tyr Leu Glu Leu Asn
        115                 120                 125

Lys Tyr Phe Phe Arg Ile Arg Lys Phe Leu Val Asn Lys Lys Tyr Ser
    130                 135                 140

Phe Cys Ala Trp Lys Ile Val Val Val Glu Ile Arg Arg Cys Phe Ser
145                 150                 155                 160

Ile Phe Tyr Lys Leu Leu Asn Met Asn
                165
```

<210> SEQ ID NO 10
<211> LENGTH: 520
<212> TYPE: DNA
<213> ORGANISM: Artificial Sequence
<220> FEATURE:
<223> OTHER INFORMATION: Description of Artificial Sequence: Rat
      IFN-like polypeptide cDNA insert and partial pAMG21 vector
      sequence
<220> FEATURE:
<221> NAME/KEY: CDS
<222> LOCATION: (4)..(510)

<400> SEQUENCE: 10

```
cat atg tgt gta tat ctc gat cat act atc ttg gag aat atg aaa ctt       48
    Met Cys Val Tyr Leu Asp His Thr Ile Leu Glu Asn Met Lys Leu
     1               5                  10                  15 ctg agc agc atc cgt acc acc ttt cct ctg cgt tgt ctg aaa gat atc       96
Leu Ser Ser Ile Arg Thr Thr Phe Pro Leu Arg Cys Leu Lys Asp Ile
```

```
                  20                      25                    30
acg gat ttt gag ttt cct caa gag att ctg ctg tac gtc cag cat gtg       144
Thr Asp Phe Glu Phe Pro Gln Glu Ile Leu Leu Tyr Val Gln His Val
             35                      40                    45 aaa aag gac atc aag gca gtc acc tat cat atc tct tct ctg gcg ctg       192
Lys Lys Asp Ile Lys Ala Val Thr Tyr His Ile Ser Ser Leu Ala Leu
         50                      55                      60 att att ttc agt ctt aaa gac tcc atc tcc ctg gcg aca gag gaa cgc       240
Ile Ile Phe Ser Leu Lys Asp Ser Ile Ser Leu Ala Thr Glu Glu Arg
     65                      70                      75 ttg gaa cgt atc cgt tct ggt ctt ttc aaa caa gtg cag caa gct cgt       288
Leu Glu Arg Ile Arg Ser Gly Leu Phe Lys Gln Val Gln Gln Ala Arg
 80                      85                      90                 95 gag tgc atg gta gac gag gag aac aag aac acg gag gag gac agt aca       336
Glu Cys Met Val Asp Glu Glu Asn Lys Asn Thr Glu Glu Asp Ser Thr
                    100                     105                   110 tca caa cat cct cac tca gag ggc ttc aag gca gtc tac ctg gaa ttg       384
Ser Gln His Pro His Ser Glu Gly Phe Lys Ala Val Tyr Leu Glu Leu
                115                     120                    125 aac aag tat ttc ttc cgt atc cgt aag ttc ctg gta aat aag aaa tac       432
Asn Lys Tyr Phe Phe Arg Ile Arg Lys Phe Leu Val Asn Lys Lys Tyr
            130                     135                    140 agt ttc tgt gcc tgg aag att gtc gtg gtg gaa att cgt cgt tct ttc       480
Ser Phe Cys Ala Trp Lys Ile Val Val Val Glu Ile Arg Arg Ser Phe
        145                     150                     155 agt att ttt tac aaa ctg ctg aac atg aat taatggatcc                    520
Ser Ile Phe Tyr Lys Leu Leu Asn Met Asn
160                     165

<210> SEQ ID NO 11
<211> LENGTH: 169
<212> TYPE: PRT
<213> ORGANISM: Artificial Sequence
<220> FEATURE:
<223> OTHER INFORMATION: Description of Artificial Sequence: Rat
      IFN-like polypeptide cDNA insert and partial pAMG21 vector
      sequence

<400> SEQUENCE: 11

Met Cys Val Tyr Leu Asp His Thr Ile Leu Glu Asn Met Lys Leu Leu
 1               5                  10                  15

Ser Ser Ile Arg Thr Thr Phe Pro Leu Arg Cys Leu Lys Asp Ile Thr
            20                  25                  30

Asp Phe Glu Phe Pro Gln Glu Ile Leu Leu Tyr Val Gln His Val Lys
        35                  40                  45

Lys Asp Ile Lys Ala Val Thr Tyr His Ile Ser Ser Leu Ala Leu Ile
    50                  55                  60

Ile Phe Ser Leu Lys Asp Ser Ile Ser Leu Ala Thr Glu Glu Arg Leu
65                  70                  75                  80

Glu Arg Ile Arg Ser Gly Leu Phe Lys Gln Val Gln Gln Ala Arg Glu
                85                  90                  95

Cys Met Val Asp Glu Glu Asn Lys Asn Thr Glu Glu Asp Ser Thr Ser
            100                 105                 110

Gln His Pro His Ser Glu Gly Phe Lys Ala Val Tyr Leu Glu Leu Asn
        115                 120                 125

Lys Tyr Phe Phe Arg Ile Arg Lys Phe Leu Val Asn Lys Lys Tyr Ser
    130                 135                 140

Phe Cys Ala Trp Lys Ile Val Val Val Glu Ile Arg Arg Ser Phe Ser
145                 150                 155                 160
```

```
Ile Phe Tyr Lys Leu Leu Asn Met Asn
            165

<210> SEQ ID NO 12
<211> LENGTH: 568
<212> TYPE: DNA
<213> ORGANISM: Artificial Sequence
<220> FEATURE:
<223> OTHER INFORMATION: Description of Artificial Sequence: Human
      IFN-like polypeptide cDNA insert and partial pAMG21 vector
      sequence
<220> FEATURE:
<221> NAME/KEY: CDS
<222> LOCATION: (22)..(558)

<400> SEQUENCE: 12
tctagaaagg aggaataaca t atg tgt aac ctg ctg aac gtt cac ctg cgt         51
                        Met Cys Asn Leu Leu Asn Val His Leu Arg
                         1               5                  10 cgt gtt acc tgg caa aat ctg aga cat ctg agt agt atg agc aat tca         99
Arg Val Thr Trp Gln Asn Leu Arg His Leu Ser Ser Met Ser Asn Ser
             15                  20                  25 ttt cct gta gaa tgt cta cga gaa aac ata gct ttt gag ttg ccc caa        147
Phe Pro Val Glu Cys Leu Arg Glu Asn Ile Ala Phe Glu Leu Pro Gln
         30                  35                  40 gag ttt ctg caa tac acc caa cct atg aag agg gac atc aag aag gcc        195
Glu Phe Leu Gln Tyr Thr Gln Pro Met Lys Arg Asp Ile Lys Lys Ala
     45                  50                  55 ttc tat gaa atg tcc cta cag gcc ttc aac atc ttc agc caa cac acc        243
Phe Tyr Glu Met Ser Leu Gln Ala Phe Asn Ile Phe Ser Gln His Thr
 60                  65                  70 ttc aaa tat tgg aaa gag aga cac ctc aaa caa atc caa ata gga ctt        291
Phe Lys Tyr Trp Lys Glu Arg His Leu Lys Gln Ile Gln Ile Gly Leu
 75                  80                  85                  90 gat cag caa gca gag tac ctg aac caa tgc ttg gag gaa gac gag aat        339
Asp Gln Gln Ala Glu Tyr Leu Asn Gln Cys Leu Glu Glu Asp Glu Asn
                 95                 100                 105 gaa aat gaa gac atg aaa gaa atg aaa gag aat gag atg aaa ccc tca        387
Glu Asn Glu Asp Met Lys Glu Met Lys Glu Asn Glu Met Lys Pro Ser
            110                 115                 120 gaa gcc agg gtc ccc cag ctg agc agc ctg gaa ctg agg aga tat ttc        435
Glu Ala Arg Val Pro Gln Leu Ser Ser Leu Glu Leu Arg Arg Tyr Phe
        125                 130                 135 cac agg ata gac aat ttc ctg aaa gaa aag aaa tac agt gac tgt gcc        483
His Arg Ile Asp Asn Phe Leu Lys Glu Lys Lys Tyr Ser Asp Cys Ala
    140                 145                 150 tgg gag att gtc cga gtg gaa atc cgt cgt tgc ctg tac tac ttt tac        531
Trp Glu Ile Val Arg Val Glu Ile Arg Arg Cys Leu Tyr Tyr Phe Tyr
155                 160                 165                 170 aaa ttt acc gct ctg ttc cgt cgt aaa taatggatcc                         568
Lys Phe Thr Ala Leu Phe Arg Arg Lys
                175

<210> SEQ ID NO 13
<211> LENGTH: 179
<212> TYPE: PRT
<213> ORGANISM: Artificial Sequence
<220> FEATURE:
<223> OTHER INFORMATION: Description of Artificial Sequence: Rat
      IFN-like polypeptide cDNA insert and partial pAMG21 vector
      sequence

<400> SEQUENCE: 13
```

-continued

```
Met Cys Asn Leu Leu Asn Val His Leu Arg Arg Val Thr Trp Gln Asn
 1               5                  10                  15

Leu Arg His Leu Ser Ser Met Ser Asn Ser Phe Pro Val Glu Cys Leu
             20                  25                  30

Arg Glu Asn Ile Ala Phe Glu Leu Pro Gln Glu Phe Leu Gln Tyr Thr
         35                  40                  45

Gln Pro Met Lys Arg Asp Ile Lys Lys Ala Phe Tyr Glu Met Ser Leu
     50                  55                  60

Gln Ala Phe Asn Ile Phe Ser Gln His Thr Phe Lys Tyr Trp Lys Glu
 65                  70                  75                  80

Arg His Leu Lys Gln Ile Gln Ile Gly Leu Asp Gln Gln Ala Glu Tyr
             85                  90                  95

Leu Asn Gln Cys Leu Glu Glu Asp Glu Asn Glu Asn Glu Asp Met Lys
            100                 105                 110

Glu Met Lys Glu Asn Glu Met Lys Pro Ser Glu Ala Arg Val Pro Gln
        115                 120                 125

Leu Ser Ser Leu Glu Leu Arg Arg Tyr Phe His Arg Ile Asp Asn Phe
    130                 135                 140

Leu Lys Glu Lys Lys Tyr Ser Asp Cys Ala Trp Glu Ile Val Arg Val
145                 150                 155                 160

Glu Ile Arg Arg Cys Leu Tyr Tyr Phe Tyr Lys Phe Thr Ala Leu Phe
                165                 170                 175

Arg Arg Lys
```

<210> SEQ ID NO 14
<211> LENGTH: 568
<212> TYPE: DNA
<213> ORGANISM: Artificial Sequence
<220> FEATURE:
<223> OTHER INFORMATION: Description of Artificial Sequence: Human
      IFN-like polypeptide cDNA insert and partial pAMG21 vector
      sequence
<220> FEATURE:
<221> NAME/KEY: CDS
<222> LOCATION: (22)..(558)

<400> SEQUENCE: 14

```
tctagaaagg aggaataaca t atg tgt aac ctg ctg aac gtt cac ctg cgt        51
                         Met Cys Asn Leu Leu Asn Val His Leu Arg
                          1               5                  10 cgt gtt acc tgg caa aat ctg aga cat ctg agt agt atg agc aat tca        99
Arg Val Thr Trp Gln Asn Leu Arg His Leu Ser Ser Met Ser Asn Ser
             15                  20                  25 ttt cct gta gaa tgt cta cga gaa aac ata gct ttt gag ttg ccc caa       147
Phe Pro Val Glu Cys Leu Arg Glu Asn Ile Ala Phe Glu Leu Pro Gln
 30                  35                  40 gag ttc ctg caa tac acc caa cct atg aag agg gac atc aag aag gcc       195
Glu Phe Leu Gln Tyr Thr Gln Pro Met Lys Arg Asp Ile Lys Lys Ala
         45                  50                  55 ttc tat gaa atg tcc cta cag gcc ttc aac atc ttc agc caa cac acc       243
Phe Tyr Glu Met Ser Leu Gln Ala Phe Asn Ile Phe Ser Gln His Thr
     60                  65                  70 ttc aaa tat tgg aaa gag aga cac ctc aaa caa atc caa ata gga ctt       291
Phe Lys Tyr Trp Lys Glu Arg His Leu Lys Gln Ile Gln Ile Gly Leu
 75                  80                  85                  90 gat cag caa gca gag tac ctg aac caa tgc ttg gag gaa gac gag aat       339
Asp Gln Gln Ala Glu Tyr Leu Asn Gln Cys Leu Glu Glu Asp Glu Asn
             95                 100                 105 gaa aat gaa gac atg aaa gaa atg aaa gag aat gag atg aaa ccc tca       387
```

```
                                                            gaa gcc agg gtc ccc cag ctg agc agc ctg gaa ctg agg aga tat ttc     435
Glu Asn Glu Asp Met Lys Glu Met Lys Glu Asn Glu Met Lys Pro Ser
        110                 115                 120
                            Glu Ala Arg Val Pro Gln Leu Ser Ser Leu Glu Leu Arg Arg Tyr Phe
                                    125                 130                 135 cac agg ata gac aat ttc ctg aaa gaa aag aaa tac agt gac tgt gcc     483
His Arg Ile Asp Asn Phe Leu Lys Glu Lys Lys Tyr Ser Asp Cys Ala
        140                 145                 150 tgg gag att gtc cga gtg gaa atc cgt cgt tct ctg tac tac ttt tac     531
Trp Glu Ile Val Arg Val Glu Ile Arg Arg Ser Leu Tyr Tyr Phe Tyr
155                 160                 165                 170 aaa ttt acc gct ctg ttc cgt cgt aaa taatggatcc                       568
Lys Phe Thr Ala Leu Phe Arg Arg Lys
                175

<210> SEQ ID NO 15
<211> LENGTH: 179
<212> TYPE: PRT
<213> ORGANISM: Artificial Sequence
<220> FEATURE:
<223> OTHER INFORMATION: Description of Artificial Sequence: Human
      IFN-like polypeptide cDNA insert and partial pAMG21 vector
      sequence

<400> SEQUENCE: 15

Met Cys Asn Leu Leu Asn Val His Leu Arg Arg Val Thr Trp Gln Asn
 1               5                  10                  15

Leu Arg His Leu Ser Ser Met Ser Asn Ser Phe Pro Val Glu Cys Leu
            20                  25                  30

Arg Glu Asn Ile Ala Phe Glu Leu Pro Gln Glu Phe Leu Gln Tyr Thr
        35                  40                  45

Gln Pro Met Lys Arg Asp Ile Lys Lys Ala Phe Tyr Glu Met Ser Leu
    50                  55                  60

Gln Ala Phe Asn Ile Phe Ser Gln His Thr Phe Lys Tyr Trp Lys Glu
65                  70                  75                  80

Arg His Leu Lys Gln Ile Gln Ile Gly Leu Asp Gln Gln Ala Glu Tyr
                85                  90                  95

Leu Asn Gln Cys Leu Glu Glu Asp Glu Asn Glu Asn Glu Asp Met Lys
            100                 105                 110

Glu Met Lys Glu Asn Glu Met Lys Pro Ser Glu Ala Arg Val Pro Gln
        115                 120                 125

Leu Ser Ser Leu Glu Leu Arg Arg Tyr Phe His Arg Ile Asp Asn Phe
    130                 135                 140

Leu Lys Glu Lys Lys Tyr Ser Asp Cys Ala Trp Glu Ile Val Arg Val
145                 150                 155                 160

Glu Ile Arg Arg Ser Leu Tyr Tyr Phe Tyr Lys Phe Thr Ala Leu Phe
                165                 170                 175

Arg Arg Lys

<210> SEQ ID NO 16
<211> LENGTH: 556
<212> TYPE: DNA
<213> ORGANISM: Artificial Sequence
<220> FEATURE:
<223> OTHER INFORMATION: Description of Artificial Sequence: Human
      IFN-like polypeptide cDNA insert and partial pAMG21 vector
      sequence
<220> FEATURE:
<221> NAME/KEY: CDS
<222> LOCATION: (1)..(546)
```

-continued

```
<400> SEQUENCE: 16 cat atg ctg gac tgt aac ctg ctg aac gtt cac ctg cgt cgt gtt acc      48
His Met Leu Asp Cys Asn Leu Leu Asn Val His Leu Arg Arg Val Thr
  1               5                  10                  15 tgg caa aat ctg aga cat ctg agt agt atg agc aat tca ttt cct gta      96
Trp Gln Asn Leu Arg His Leu Ser Ser Met Ser Asn Ser Phe Pro Val
             20                  25                  30 gaa tgt cta cga gaa aac ata gct ttt gag ttg ccc caa gag ttt ctg     144
Glu Cys Leu Arg Glu Asn Ile Ala Phe Glu Leu Pro Gln Glu Phe Leu
         35                  40                  45 caa tac acc caa cct atg aag agg gac atc aag aag gcc ttc tat gaa     192
Gln Tyr Thr Gln Pro Met Lys Arg Asp Ile Lys Lys Ala Phe Tyr Glu
 50                  55                  60 atg tcc cta cag gcc ttc aac atc ttc agc caa cac acc ttc aaa tat     240
Met Ser Leu Gln Ala Phe Asn Ile Phe Ser Gln His Thr Phe Lys Tyr
 65                  70                  75                  80 tgg aaa gag aga cac ctc aaa caa atc caa ata gga ctt gat cag caa     288
Trp Lys Glu Arg His Leu Lys Gln Ile Gln Ile Gly Leu Asp Gln Gln
                 85                  90                  95 gca gag tac ctg aac caa tgc ttg gag gaa gac gag aat gaa aat gaa     336
Ala Glu Tyr Leu Asn Gln Cys Leu Glu Glu Asp Glu Asn Glu Asn Glu
            100                 105                 110 gac atg aaa gaa atg aaa gag aat gag atg aaa ccc tca gaa gcc agg     384
Asp Met Lys Glu Met Lys Glu Asn Glu Met Lys Pro Ser Glu Ala Arg
        115                 120                 125 gtc ccc cag ctg agc agc ctg gaa ctg agg aga tat ttc cac agg ata     432
Val Pro Gln Leu Ser Ser Leu Glu Leu Arg Arg Tyr Phe His Arg Ile
    130                 135                 140 gac aat ttc ctg aaa gaa aag aaa tac agt gac tgt gcc tgg gag att     480
Asp Asn Phe Leu Lys Glu Lys Lys Tyr Ser Asp Cys Ala Trp Glu Ile
145                 150                 155                 160 gtc cga gtg gaa atc cgt cgt tgc ctg tac tac ttt tac aaa ttt acc     528
Val Arg Val Glu Ile Arg Arg Cys Leu Tyr Tyr Phe Tyr Lys Phe Thr
                165                 170                 175 gct ctg ttc cgt cgt aaa taatggatcc                                  556
Ala Leu Phe Arg Arg Lys
            180

<210> SEQ ID NO 17
<211> LENGTH: 182
<212> TYPE: PRT
<213> ORGANISM: Artificial Sequence
<220> FEATURE:
<223> OTHER INFORMATION: Description of Artificial Sequence: Human
      IFN-like polypeptide cDNA insert and partial pAMG21 vector
      sequence

<400> SEQUENCE: 17

His Met Leu Asp Cys Asn Leu Leu Asn Val His Leu Arg Arg Val Thr
  1               5                  10                  15

Trp Gln Asn Leu Arg His Leu Ser Ser Met Ser Asn Ser Phe Pro Val
             20                  25                  30

Glu Cys Leu Arg Glu Asn Ile Ala Phe Glu Leu Pro Gln Glu Phe Leu
         35                  40                  45

Gln Tyr Thr Gln Pro Met Lys Arg Asp Ile Lys Lys Ala Phe Tyr Glu
 50                  55                  60

Met Ser Leu Gln Ala Phe Asn Ile Phe Ser Gln His Thr Phe Lys Tyr
 65                  70                  75                  80

Trp Lys Glu Arg His Leu Lys Gln Ile Gln Ile Gly Leu Asp Gln Gln
                 85                  90                  95
```

```
Ala Glu Tyr Leu Asn Gln Cys Leu Glu Glu Asp Glu Asn Glu
            100                 105                 110

Asp Met Lys Glu Met Lys Glu Asn Glu Met Lys Pro Ser Glu Ala Arg
        115                 120                 125

Val Pro Gln Leu Ser Ser Leu Glu Leu Arg Arg Tyr Phe His Arg Ile
    130                 135                 140

Asp Asn Phe Leu Lys Glu Lys Lys Tyr Ser Asp Cys Ala Trp Glu Ile
145                 150                 155                 160

Val Arg Val Glu Ile Arg Arg Cys Leu Tyr Tyr Phe Tyr Lys Phe Thr
                165                 170                 175

Ala Leu Phe Arg Arg Lys
            180

<210> SEQ ID NO 18
<211> LENGTH: 11
<212> TYPE: PRT
<213> ORGANISM: Human immunodeficiency virus type 1

<400> SEQUENCE: 18

Tyr Gly Arg Lys Lys Arg Arg Gln Arg Arg Arg
 1               5                  10

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence:
      Internalizing domain derived from HIV tat protein

<400> SEQUENCE: 19

Gly Gly Gly Gly Tyr Gly Arg Lys Lys Arg Arg Gln Arg Arg Arg
 1               5                  10                  15

<210> SEQ ID NO 20
<211> LENGTH: 21
<212> TYPE: DNA
<213> ORGANISM: Rattus norvegicus

<400> SEQUENCE: 20
atgacactga agtatttatg g                                           21

<210> SEQ ID NO 21
<211> LENGTH: 21
<212> TYPE: DNA
<213> ORGANISM: Rattus norvegicus

<400> SEQUENCE: 21
attcatgttg agtagtttgt a                                           21

<210> SEQ ID NO 22
<211> LENGTH: 48
<212> TYPE: DNA
<213> ORGANISM: Artificial Sequence
<220> FEATURE:
<223> OTHER INFORMATION: Description of Artificial Sequence: PCR primer
      1825-22

<400> SEQUENCE: 22
gaataacata tgtgtgtata tctcgatcat actatcttgg agaatatg              48

<210> SEQ ID NO 23
```

```
<211> LENGTH: 63
<212> TYPE: DNA
<213> ORGANISM: Artificial Sequence
<220> FEATURE:
<223> OTHER INFORMATION: Description of Artificial Sequence: PCR primer
      1825-21

<400> SEQUENCE: 23
ccgcggatcc attaattcat gttcagcagt ttgtaaaaaa tactgaaaca acgacgaatt    60
tcc                                                                  63

<210> SEQ ID NO 24
<211> LENGTH: 63
<212> TYPE: DNA
<213> ORGANISM: Artificial Sequence
<220> FEATURE:
<223> OTHER INFORMATION: Description of Artificial Sequence: PCR primer
      1909-56

<400> SEQUENCE: 24
ccgcggatcc attaattcat gttcagcagt ttgtaaaaaa tactgaaaga acgacgaatt    60
tcc                                                                  63

<210> SEQ ID NO 25
<211> LENGTH: 67
<212> TYPE: DNA
<213> ORGANISM: Artificial Sequence
<220> FEATURE:
<223> OTHER INFORMATION: Description of Artificial Sequence: PCR primer
      1967-32

<400> SEQUENCE: 25
ttgatctaga aaggaggaat aacatatgtg taacctgctg aacgttcacc tgcgtcgtgt    60
tacctgg                                                              67

<210> SEQ ID NO 26
<211> LENGTH: 71
<212> TYPE: DNA
<213> ORGANISM: Artificial Sequence
<220> FEATURE:
<223> OTHER INFORMATION: Description of Artificial Sequence: PCR primer
      1982-14

<400> SEQUENCE: 26
ccgcggatcc attatttacg acggaacaga gcggtaaatt tgtaaaagta gtacaggcaa    60
cgacgatttc c                                                         71

<210> SEQ ID NO 27
<211> LENGTH: 72
<212> TYPE: DNA
<213> ORGANISM: Artificial Sequence
<220> FEATURE:
<223> OTHER INFORMATION: Description of Artificial Sequence: PCR primer
      1967-33

<400> SEQUENCE: 27
ccgcggatcc attatttacg acggaacaga gcggtaaatt tgtaaaagta gtacagagaa    60
cgacggattt cc                                                        72

<210> SEQ ID NO 28
<211> LENGTH: 39
<212> TYPE: DNA
<213> ORGANISM: Artificial Sequence
<220> FEATURE:
```

<223> OTHER INFORMATION: Description of Artificial Sequence: PCR primer
      2103-87

<400> SEQUENCE: 28
aaggagcata tgctggactg taacctgctg aacgttcac                              39

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: PCR primer
      1200-54

<400> SEQUENCE: 29
gttattgctc agcggtggca                                                   20

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: PCR primer
      1847-77

<400> SEQUENCE: 30
cccaagctta ccatgacact gaagtattta tg                                     32

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: PCR primer
      1847-78

<400> SEQUENCE: 31
aaggaaaaaa gcggccgcat tcatgttgag tag                                    33

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: PCR primer
      1896-56

<400> SEQUENCE: 32
acgcgtcgac tcatcaattc atgttgagta gtttg                                  35

<210> SEQ ID NO 33
<211> LENGTH: 39
<212> TYPE: DNA
<213> ORGANISM: Artificial Sequence
<220> FEATURE:
<223> OTHER INFORMATION: Description of Artificial Sequence: PCR primer
      1896-57

<400> SEQUENCE: 33
aaggaaaaaa gcggccgctc atcaattcat gttgagtag                              39

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: PCR primer
      1954-45

<400> SEQUENCE: 34
acgcgtcgac ttattatttc ctcctgaata g                                      31

<210> SEQ ID NO 35
<211> LENGTH: 42
<212> TYPE: DNA
<213> ORGANISM: Artificial Sequence
<220> FEATURE:
<223> OTHER INFORMATION: Description of Artificial Sequence: PCR primer
      1954-46

<400> SEQUENCE: 35
aaggaaaaaa gcggccgctt attatttcct cctgaataga gc                          42

<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: PCR primer
      1955-44

<400> SEQUENCE: 36
cccaagctta ccatgagcac caaacctgat atg                                    33

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: PCR primer
      1954-47

<400> SEQUENCE: 37
cccaagctta ccatgattca aaagtgtttg tggc                                   34

<210> SEQ ID NO 38
<211> LENGTH: 53
<212> TYPE: DNA
<213> ORGANISM: Artificial Sequence
<220> FEATURE:
<223> OTHER INFORMATION: Description of Artificial Sequence: PCR primer
      1954-48

<400> SEQUENCE: 38
aaggaaaaaa gcggccgcgc ggccctcgat tttcctcctg aatagagctg taa              53

<210> SEQ ID NO 39
<211> LENGTH: 41
<212> TYPE: DNA
<213> ORGANISM: Artificial Sequence
<220> FEATURE:
<223> OTHER INFORMATION: Description of Artificial Sequence: PCR primer
      1954-49

<400> SEQUENCE: 39
aaggaaaaaa gcggccgctt tcctcctgaa tagagctgta a                           41